(12) United States Patent
Patience

(10) Patent No.: US 6,867,347 B2
(45) Date of Patent: Mar. 15, 2005

(54) SWINE DEFECTIVE FOR TRANSMISSION OF PORCINE ENDOGENOUS RETROVIRUS AND USES THEREOF

(75) Inventor: Clive Patience, Beverly, MA (US)

(73) Assignee: Immerge Biotherapeutics, Cambridge, MA (US)

( * ) Notice: Subject to any disclaimer, the term of this patent is extended or adjusted under 35 U.S.C. 154(b) by 0 days.

(21) Appl. No.: 09/766,154

(22) Filed: Jan. 19, 2001

(65) Prior Publication Data

US 2002/0010948 A1 Jan. 24, 2002

Related U.S. Application Data

(60) Provisional application No. 60/243,695, filed on Oct. 27, 2000, provisional application No. 60/182,965, filed on Feb. 16, 2000, and provisional application No. 60/177,003, filed on Jan. 19, 2000.

(51) Int. Cl.[7] .......................... A01K 67/02; C12Q 1/68; C12N 5/06
(52) U.S. Cl. ............................... 800/8; 435/6; 435/435
(58) Field of Search .......................... 800/8; 435/6, 325

(56) References Cited

U.S. PATENT DOCUMENTS

| | | | |
|---|---|---|---|
| 5,876,708 A | 3/1999 | Sachs | 424/93.1 |
| 6,006,752 A | 12/1999 | Sykes | 128/898 |
| 6,100,034 A | 8/2000 | Stoye et al. | 435/6 |

OTHER PUBLICATIONS

Kaeffer et.al.; Histocompatible Miniature Pig (d/d haplotype): Generation of Hybridomas Secreting A or M Monoclonal Antibody, 1991, Hybridoma, vol. 10: 731–744.*
Wilson et al., J. of Virology, vol. 72, pp. 3082–3087 (1998).
Fishman, J. A., Xenotransplantation, vol. 1, pp. 47–57 (1994).
Lovatt, et al., "High throughput detection of retrovirus–associated transcriptase using an improved fluorescent product enhanced reverse Transcriptase Assay and its Comparison to Conventional Detection Methods," Journal of Virological Methods, pp. 185–200 (1999).
Wilson, et al., "Extended Analysis of the In Vitro Tropism of Porcine Endogenous Retrovirus," Journal of Virology, vol. 74, No. 1, pp. 49–56 (Jan. 2000).
Czauderna, et al., "Establishment and Characterization of Molecular Clones of Porcine Endogenous Retroviruses Replicating on Human Cells," Journal of Virology, vol. 74, No. 9, pp. 4028–4038 (May 2000).

Deng, et al., "Transmission of Porcine Endogenous Retroviruses in Severe Combined Immunodeficient Mice . . . ," vol. 70, No. 7, pp. 1010–1016 (Oct. 2000).
Pitkin, et al., "Evidence of Absence of Porcine Endogenous Retrovirus (PERV) Infection in Patients Treated with a Bioartificial Liver Support System," Blackwell Science, Inc., pp. 829–833, (1999).
Patience, et al., "Infection of Human Cells by an Endogenous Retrovirus of Pigs," Nature Medicine, vol. 3, No. 3 (Mar. 1997).
Blusch, et al., "Infection of Nonhuman Primate Cells by Pig Endogenous Retrovirus," Journal of Virology, vol. 74, No. 16, pp. 7687–7690 (Aug. 2000).
van der Laan, et al., "Infection by Porcine Endogenous Retrovirus After Islet Xenotransplantation in SCID Mice," Nature, vol. 407, (Sep. 2000).
Bosch, et al., "Study of Full–Length Porcine Endogenous Retrovirus Genomes with Envelope Gene Polymorphism in a Specific–Pathogen–Free Large White Swine Herd," Journal of Virology, vol. 74, No. 18, pp. 8575–8581 (Sep. 2000).
Jeffrey L. Platt, "New Risks, New Gains," Nature, vol. 407, pp. 27–29, (Sep. 2000).
Dinsmore, et al., "No Evidence for Infection of Human Cells with Porcine Endogenous Retrovirus (PERV) After Exposure to Porcine Fetal Neuronal Cells," Transplantation, vol. 70, No. 9, pp. 1382–1389 (Nov. 15, 2000).
Paradis, et al., "Search for Cross–Species Transmission of Porcine Endogenous Retrovirus in Patients Treated with Living Pig Tissue," Science, vol. 285, pp. 1236–1241, (Aug. 20, 1999).

* cited by examiner

*Primary Examiner*—Anne Marie S. Wehbé
(74) *Attorney, Agent, or Firm*—Elliot M. Olstein; Alan J. Grant

(57) ABSTRACT

Miniature swine whose genomes contain sequences characteristic of pig endogenous retrovirus genes but which are non-infectious to humans are disclosed as sources of organs, tissues and cells for introduction into human recipients afflicted with diseases, or at risk of diseases, whose etiology involves the presence of inadequately functioning organs and for which xenotransplantation of such organs, tissues and cells would have a palliative effect. Methods of producing such animals and for screening animals for the desired properties are also disclosed.

14 Claims, 12 Drawing Sheets

FIGURE 3(a)   Sequence of clone 12002-1

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GGACAGCCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCTC 350
AGGACCCCCA AATAATGAAG AATATTGCGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGAC 600
```

FIGURE 3(b)   Sequence of clone 12002-2

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GGACAGCCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGAC 600
```

FIGURE 3(c)   Sequence of clone 12002-3

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GGACAGCCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT
```

FIGURE 3(d)    Sequence of clone 12002-4

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GAACAGTCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGAC 600
```

FIGURE 3(e)    Sequence of clone 12002-5

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GAACAGTCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGA
```

FIGURE 3(f)    Sequence of clone 12002-6

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GAACAGTCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGA
```

FIGURE 3(g)    Sequence of clone 12002-7

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GAACAGTCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCCA ATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGAC 600
```

FIGURE 4    Comparison of sequences of clones 12002-1 though 12002-7

| | | |
|---|---|---|
| 12002-1.DNA | 1 ATGCATCCCA CGTTAAGCCG GCGCCACCTC CCGATTCGGG GTGGAAAGCC | 50 |
| 12002-2.DNA | 1 ATGCATCCCA CGTTAAGCCG GCGCCACCTC CCGATTCGGG GTGGAAAGCC | 50 |
| 12002-3.DNA | 1 ATGCATCCCA CGTTAAGCCG GCGCCACCTC CCGATTCGGG GTGGAAAGCC | 50 |
| 12002-4.DNA | 1 ATGCATCCCA CGTTAAGCCG GCGCCACCTC CCGATTCGGG GTGGAAAGCC | 50 |
| 12002-5.DNA | 1 ATGCATCCCA CGTTAAGCCG GCGCCACCTC CCGATTCGGG GTGGAAAGCC | 50 |
| 12002-6.DNA | 1 ATGCATCCCA CGTTAAGCCG GCGCCACCTC CCGATTCGGG GTGGAAAGCC | 50 |
| 12002-7.DNA | 1 ATGCATCCCA CGTTAAGCCG GCGCCACCTC CCGATTCGGG GTGGAAAGCC | 50 |
| 12002-1.DNA | 51 GAAAAGACTG AAAATCCCCT TAAGCTTCGC CTCCATCGCG TGGTTCCTTA | 100 |
| 12002-2.DNA | 51 GAAAAGACTG AAAATCCCCT TAAGCTTCGC CTCCATCGCG TGGTTCCTTA | 100 |
| 12002-3.DNA | 51 GAAAAGACTG AAAATCCCCT TAAGCTTCGC CTCCATCGCG TGGTTCCTTA | 100 |
| 12002-4.DNA | 51 GAAAAGACTG AAAATCCCCT TAAGCTTCGC CTCCATCGCG TGGTTCCTTA | 100 |
| 12002-5.DNA | 51 GAAAAGACTG AAAATCCCCT TAAGCTTCGC CTCCATCGCG TGGTTCCTTA | 100 |
| 12002-6.DNA | 51 GAAAAGACTG AAAATCCCCT TAAGCTTCGC CTCCATCGCG TGGTTCCTTA | 100 |
| 12002-7.DNA | 51 GAAAAGACTG AAAATCCCCT TAAGCTTCGC CTCCATCGCG TGGTTCCTTA | 100 |
| 12002-1.DNA | 101 CTCTGTCAAT AACTCCTCAA GTTAATGGTA AACGCCTTGT GGACAGCCCG | 150 |
| 12002-2.DNA | 101 CTCTGTCAAT AACTCCTCAA GTTAATGGTA AACGCCTTGT GGACAGCCCG | 150 |
| 12002-3.DNA | 101 CTCTGTCAAT AACTCCTCAA GTTAATGGTA AACGCCTTGT GGACAGCCCG | 150 |
| 12002-4.DNA | 101 CTCTGTCAAT AACTCCTCAA GTTAATGGTA AACGCCTTGT GAACAGTCCG | 150 |
| 12002-5.DNA | 101 CTCTGTCAAT AACTCCTCAA GTTAATGGTA AACGCCTTGT GAACAGTCCG | 150 |
| 12002-6.DNA | 101 CTCTGTCAAT AACTCCTCAA GTTAATGGTA AACGCCTTGT GAACAGTCCG | 150 |
| 12002-7.DNA | 101 CTCTGTCAAT AACTCCTCAA GTTAATGGTA AACGCCTTGT GAACAGTCCG | 150 |
| 12002-1.DNA | 151 AACTCCCATA AACCCTTATC TCTCACCTGG TTACTTACTG ACTCCGGTAC | 200 |
| 12002-2.DNA | 151 AACTCCCATA AACCCTTATC TCTCACCTGG TTACTTACTG ACTCCGGTAC | 200 |
| 12002-3.DNA | 151 AACTCCCATA AACCCTTATC TCTCACCTGG TTACTTACTG ACTCCGGTAC | 200 |
| 12002-4.DNA | 151 AACTCCCATA AACCCTTATC TCTCACCTGG TTACTTACTG ACTCCGGTAC | 200 |
| 12002-5.DNA | 151 AACTCCCATA AACCCTTATC TCTCACCTGG TTACTTACTG ACTCCGGTAC | 200 |
| 12002-6.DNA | 151 AACTCCCATA AACCCTTATC TCTCACCTGG TTACTTACTG ACTCCGGTAC | 200 |
| 12002-7.DNA | 151 AACTCCCATA AACCCTTATC TCTCACCTGG TTACTTACTG ACTCCGGTAC | 200 |
| 12002-1.DNA | 201 AGGTATTAAT ATTAACAGCA CTCAAGGGGA GGCTCCCTTG GGGACCTGGT | 250 |
| 12002-2.DNA | 201 AGGTATTAAT ATTAACAGCA CTCAAGGGGA GGCTCCCTTG GGGACCTGGT | 250 |
| 12002-3.DNA | 201 AGGTATTAAT ATTAACAGCA CTCAAGGGGA GGCTCCCTTG GGGACCTGGT | 250 |
| 12002-4.DNA | 201 AGGTATTAAT ATTAACAGCA CTCAAGGGGA GGCTCCCTTG GGGACCTGGT | 250 |
| 12002-5.DNA | 201 AGGTATTAAT ATTAACAGCA CTCAAGGGGA GGCTCCCTTG GGGACCTGGT | 250 |
| 12002-6.DNA | 201 AGGTATTAAT ATTAACAGCA CTCAAGGGGA GGCTCCCTTG GGGACCTGGT | 250 |
| 12002-7.DNA | 201 AGGTATTAAT ATTAACAGCA CTCAAGGGGA GGCTCCCTTG GGGACCTGGT | 250 |
| 12002-1.DNA | 251 GGCCTGAATT ATATGTCTGC CTTCGATCAG TAATCCCTGG TCTCAATGAC | 300 |
| 12002-2.DNA | 251 GGCCTGAATT ATATGTCTGC CTTCGATCAG TAATCCCTGG TCTCAATGAC | 300 |
| 12002-3.DNA | 251 GGCCTGAATT ATATGTCTGC CTTCGATCAG TAATCCCTGG TCTCAATGAC | 300 |
| 12002-4.DNA | 251 GGCCTGAATT ATATGTCTGC CTTCGATCAG TAATCCCTGG TCTCAATGAC | 300 |
| 12002-5.DNA | 251 GGCCTGAATT ATATGTCTGC CTTCGATCAG TAATCCCTGG TCTCAATGAC | 300 |
| 12002-6.DNA | 251 GGCCTGAATT ATATGTCTGC CTTCGATCAG TAATCCCTGG TCTCAATGAC | 300 |
| 12002-7.DNA | 251 GGCCTGAATT ATATGTCTGC CTTCGATCAG TAATCCCTGG TCTCAATGAC | 300 |
| 12002-1.DNA | 301 CAGGCCACAC CCCCCGATGT ACTCCGTGCT TACGGGTTTT ACGTTTGCTC | 350 |
| 12002-2.DNA | 301 CAGGCCACAC CCCCCGATGT ACTCCGTGCT TACGGGTTTT ACGTTTGCCC | 350 |
| 12002-3.DNA | 301 CAGGCCACAC CCCCCGATGT ACTCCGTGCT TACGGGTTTT ACGTTTGCCC | 350 |
| 12002-4.DNA | 301 CAGGCCACAC CCCCCGATGT ACTCCGTGCT TACGGGTTTT ACGTTTGCCC | 350 |
| 12002-5.DNA | 301 CAGGCCACAC CCCCCGATGT ACTCCGTGCT TACGGGTTTT ACGTTTGCCC | 350 |
| 12002-6.DNA | 301 CAGGCCACAC CCCCCGATGT ACTCCGTGCT TACGGGTTTT ACGTTTGCCC | 350 |
| 12002-7.DNA | 301 CAGGCCACAC CCCCCGATGT ACTCCGTGCT TACGGGTTTT ACGTTTGCCC | 350 |
| 12002-1.DNA | 351 AGGACCCCCA AATAATGAAG AATATTGCGG AAATCCTCAG GATTTCTTTT | 400 |
| 12002-2.DNA | 351 AGGACCCCCA AATAATGAAG AATATTGTGG AAATCCTCAG GATTTCTTTT | 400 |
| 12002-3.DNA | 351 AGGACCCCCA AATAATGAAG AATATTGTGG AAATCCTCAG GATTTCTTTT | 400 |
| 12002-4.DNA | 351 AGGACCCCCA AATAATGAAG AATATTGTGG AAATCCTCAG GATTTCTTTT | 400 |
| 12002-5.DNA | 351 AGGACCCCCA AATAATGAAG AATATTGTGG AAATCCTCAG GATTTCTTTT | 400 |
| 12002-6.DNA | 351 AGGACCCCCA AATAATGAAG AATATTGTGG AAATCCTCAG GATTTCTTTT | 400 |
| 12002-7.DNA | 351 AGGACCCCCA AATAATGAAG AATATTGTGG AAATCCTCAG GATTTCTTTT | 400 |

Figure 4 (cont'd)

```
12002-1.DNA    401 GCAAGCAATG GAGCTGCGTA ACTTCTAATG ATGGGAATTG GAAATGGCCA    450
12002-2.DNA    401 GCAAGCAATG GAGCTGCGTA ACTTCTAATG ATGGGAATTG GAAATGGCCA    450
12002-3.DNA    401 GCAAGCAATG GAGCTGCGTA ACTTCTAATG ATGGGAATTG GAAATGGCCA    450
12002-4.DNA    401 GCAAGCAATG GAGCTGCGTA ACTTCTAATG ATGGGAATTG GAAATGGCCA    450
12002-5.DNA    401 GCAAGCAATG GAGCTGCGTA ACTTCTAATG ATGGGAATTG GAAATGGCCA    450
12002-6.DNA    401 GCAAGCAATG GAGCTGCGTA ACTTCTAATG ATGGGAATTG GAAATGGCCA    450
12002-7.DNA    401 GCAAGCAATG GAGCTGCGTA ACTTCTAATG ATGGGAATTG GAAATGGCCA    450

12002-1.DNA    451 GTCTCTCAGC AAGACAGAGT AAGTTACTCT TTTGTTAACA ATCCTACCAG    500
12002-2.DNA    451 GTCTCTCAGC AAGACAGAGT AAGTTACTCT TTTGTTAACA ATCCTACCAG    500
12002-3.DNA    451 GTCTCTCAGC AAGACAGAGT AAGTTACTCT TTTGTTAACA ATCCTACCAG    500
12002-4.DNA    451 GTCTCTCAGC AAGACAGAGT AAGTTACTCT TTTGTTAACA ATCCTACCAG    500
12002-5.DNA    451 GTCTCTCAGC AAGACAGAGT AAGTTACTCT TTTGTTAACA ATCCTACCAG    500
12002-6.DNA    451 GTCTCTCAGC AAGACAGAGT AAGTTACTCT TTTGTTAACA ATCCTACCAG    500
12002-7.DNA    451 GTCTCTCAGC AAGACAGAGT AAGTTACTCT TTTGTTAACA ATCCTACCAG    500

12002-1.DNA    501 TTATAATCAA TTTAATTATG GCCATGGGAG ATGGAAAGAT TGGCAACAGC    550
12002-2.DNA    501 TTATAATCAA TTTAATTATG GCCATGGGAG ATGGAAAGAT TGGCAACAGC    550
12002-3.DNA    501 TTATAATCAA TTTAATTATG GCCATGGGAG ATGGAAAGAT ----------    550
12002-4.DNA    501 TTATAATCAA TTTAATTATG GCCATGGGAG ATGGAAAGAT TGGCAACAGC    550
12002-5.DNA    501 TTATAATCAA TTTAATTATG GCCATGGGAG ATGGAAAGAT TGGCAACAGC    550
12002-6.DNA    501 TTATAATCAA TTTAATTATG GCCATGGGAG ATGGAAAGAT TGGCAACAGC    550
12002-7.DNA    501 TTATAATCAA TTTAATTATG GCCATGGGAG ATGGAAAGAT TGGCAACAGC    550

12002-1.DNA    551 GGGTACAAAA AGATGTACGA AATAAGCAAA TAAGCTGTCA TTCGTTAGAC    600
12002-2.DNA    551 GGGTACAAAA AGATGTACGA AATAAGCAAA TAAGCTGTCA TTCGTTAGAC    600
12002-3.DNA    551 ---------- ---------- ---------- ---------- ----------    600
12002-4.DNA    551 GGGTACAAAA AGATGTACGA AATAAGCAAA TAAGCTGTCA TTCGTTAGAC    600
12002-5.DNA    551 GGGTACAAAA AGATGTACGA AATAAGCAAA TAAGCTGTCA TTCGTTAGA-    600
12002-6.DNA    551 GGGTACAAAA AGATGTACGA AATAAGCAAA TAAGCTGTCA TTCGTTAGA-    600
12002-7.DNA    551 GGGTACAAAA AGATGTACGA AATAAGCAAA TAAGCTGTCA TTCGTTAGAC    600
```

FIGURE 5(a)    Sequence from 11619-1

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GGACAGCCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGA
```

FIGURE 5(b)  Sequence from 11619-2

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GGACAGCCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG CCTCAATGAC 300
CAGGCCACAC CCCCGATGT ACTCCGTGCT TACGGGTTTT ACGTTTGCCC 350
AGGACCCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGA
```

FIGURE 5(c)  Sequence from 11619-3

```
ATGCATCCCA CGTTAAGCCG GCGCCACCTC CCGATTCGGG GTGGAAAGCC 50
GAAAAGACTG AAAATCCCCT TAAGCTTCGC CTCCATCGCG TGGTTCCTTA 100
CTCTGTCAAT AACTCCTCAA GTTAATGGTA AACGCCTTGT GGACAGCCCG 150
AACTCCCATA AACCCTTATC TCTCACCTGG TTACTTACTG ACTCCGGTAC 200
AGGTATTAAT ATTAACAGCA CTCAAGGGGA GGCTCCCTTG GGGACCTGGT 250
GGCCTGAATT ATATGTCTGC CTTCGATCAG TAATCCCTGG TCTCAATGAC 300
CAGGCCACAC CCCCGATGT ACTCCGTGCT TACGGGTTTT ACGTTTGCCC 350
AGGACCCCCA AATAATGAAG AATATTGTGG AAATCCTCAG GATTTCTTTT 400
GCAAGCAATG GAGCTGCGTA ACTTCTAATG ATGGGAATTG GAAATGGCCA 450
GTCTCTCAGC AAGACAGAGT AAGTTACTCT TTTGTTAACA ATCCTACCAG 500
TTATAATCAA TTTAATTATG GCCATGGGAG ATGGAAAGAT TGGCAACAGC 550
GGGTACAAAA AGATGTACGA AATAAGCAAA TAAGCTGTCA TTCGTTAGA
```

FIGURE 5(d) Sequence from 11619-4

```
GACAGCCCGA ACTCCCATAA ACCCTCATCT CTCACCTGGT TACTTACTGA  50
CTCCGGTACA GGTATTAATA TTAACAGCAC TCAAGGGGAG GCTCCCTTGG 100
GGACCTGGTG GCCTGAATTA TATGTCTGCC TTCGATCAGT AATCCCTGGT 150
CTCAATGACC AGGCCACACC CCCCGATGTA CTCCGTGCTT ACGGGTTTTA 200
CGTTTGCCCA GGACCCCAA ATAATGAAGA ATATTGTGGA AATCCTCAGG 250
ATTTCTTTTG CAAGCAATGG AGCTGCGTAA CTTCTAATGA TGGGAATTGG 300
AAATGGCCAG TCTCTCAGCA AGACAGAGTA AGTTACTCTT TTGTTAACAA 350
TCCTACCTAT AATAATCAAT TTAATTATGG CCATGGGAGA TGGAAAGATT 400
GGCAACAGCG GGTACAAAAA GATGTACGAA ATAAGCAAAT AAGCTGTCAT 450
TCGTTAGA
```

FIGURE 5(e) Sequence from 11619-5

```
TTAATGGTAA ACGCCTTGTG GACAGCCCGA ACTCCCATAA ACCCTTATCT  50
CTCACCTGGT TACTTACTGA CTCCGGTACA GGTATTAATA TTAACAGCAC 100
TCAAGGGGAG GCTCCCTTGG GGACCTGGTG GCCTGAATTA TATGTCTGCC 150
TTCGATCAGT AATCCCTGGT CTCAATGACC AGGCCACACC CCCCGATGTA 200
CTCCGTGCTT ACGGGTTTTA CGTTTGCCCA GGACCCCCAA ATAATGAAGA 250
ATATTGTGGA AATCCTCAGG ATTTCTTTTG CAGGCAATGG AGCTGCGTAA 300
CTTCTAATGA TGGAAATTGG AAATGGCCAG TCTCTCAGCA AGACAGAGTA 350
AGTTACTCTT TTGTTAACAA TCCTACCAGT TATAATCAAT TTAATTATGG 400
CCATGGGAGA TGGAAAGATT GGCAACAGCG GGTACAAAAA GATGTACGAA 450
ATAAGCAAAT AAGCTGTCAT TCGTTAGA
```

FIGURE 5(f) Sequence from 11619-6

```
TTAATGGTAA ACGCCTTGTG GACAGCCCGA ACTCCCATAA ACCCTTATCT  50
CTCACCTGGT TACTTACTGA CTCCGGTACA GGTATTAATA TTAACAGCAC 100
TCAAGGGGAG GCTCCCTTGG GGACCTGGTG GCCTGAATTA TATGTCTGCC 150
TTCGATCAGT AATCCCTGGT CTCAATGACC AGGCCACACC CCCCGATGTA 200
CTCCGTGCTT ACGGGTTTTA CGTTTGCCCA GGACCCCAA ATAATGAAGA 250
ATATTGTGGA AATCCTCAGG ATTTCTTTTG CAAGCAATGG AGCTGCGTAA 300
CTTCTAATGA TGGGAATTGG AAATGGCCAG TCTCTCAGCA AGACAGAGTA 350
AGTTACTCTT TTGTTAACAA TCCTACCAGT TATAATCAAT TTAATTATGG 400
CCATGGGAGA TGGAAAGATT GGCAACAGCG GGTACAAAAA GATGTACGAA 450
ATAAGCAAAT AAGCTGTCAT TCGTTAGA
```

FIGURE 5(g)  Sequence from 11619-7

```
GACAGCCCGA ACTCCCATAA ACCCTTATCT CTCACCTGGT TACTTACTGA  50
CTCCGGTACA GGTATTAATA TTAACAGCAC TCAAGGGGAG GCTCCCTTGG 100
GGACCTGGTG GCCTGAATTA TATGTCTGCC TTCGATCAGT AATCCCTGGT 150
CTCAATGACC AGGCCACACC CCCCGATGTA CTCCGTGCTT ACGGGTTTTA 200
CGTTTGCCCA GGACCCCAA ATAATGAAGA ATATTGTGGA AATCCTCAGG 250
ATTTCTTTTG CAAGCAATGG AGCTGCGTAA CTTCTAATGA TGGGAATTGG 300
AAATGGCCAG TCTCTCAGCA AGACAGAGTA AGTTACTCTT TTGTTAACAA 350
TCCTACCAGT TATAATCAAT TTAATTATGG CCATGGGAGA TGGAAAGATT 400
GGCAACAGCG GGTACAAAAA GATGTACGAA ATAAGCAAAT AAGCTGTCAT 450
TCGTTAGA
```

FIGURE 5(h)  Sequence from 11619-8

```
TTAATGGTAA ACGCCTTGTG GACAGCCCGA ACTCCCATAA ACCCTTATCT  50
CTCACCTGGT TACTTACTGA CTCCGGTACA GGTATTAATA TTAACAGCAC 100
TCAAGAGGAG GCTCCCTTGG GGACCTGGTG GCCTGAATTA TATGTCTGCC 150
TTCGATCAGT AATCCCTGGT CTCAATGACC AGGCCACACC CCCCGATGTA 200
CTCCGTGCTT ACGGGTTTTA CGTTTGCCCA GGACCCCAA ATAATGAAGA 250
ATATTGTGGA AATCCTCAGG ATTTCTTTTG CAAGCAATGG AGCTGCGTAA 300
CTTCTAATGA TGGGAATTGG AAATGGCCAG TCTCTCAGCA AGACAGAGTA 350
AGTTACTCTT TTGTTAACAA TCCTACCAGT TATAATCAAT TTAATTATGG 400
CCATGGGAGA TGGAAAGATT GGCAACAGCG GGTACAAAAA GATGTACGAA 450
ATAAGCAAAT AAGCTGTCAT TCGTTAGA
```

FIGURE 5(i)  Sequence from 11619-9

```
TTAATGGTAT GCGCCTTGTG GACTGCCCGA ACTCCCATAA ACCCTTATCT  50
CTCACCTGGT TACTTACTGA CTCCGGTACA GGTATTAATA TTAACATCAC 100
TCAAGGGGAG GCTCCCTTGG GGACCTGGTG GCCTGAATTA TATGTCTGCC 150
TTCGATCAGT AATCCCTGGT CTCAATGACC AGGCCACACC CCCCGATGTA 200
CTCCGTGCTT ACGGGTTTTA CGTTTGCCCA GGACCCCAA ATAATGAAGA 250
ATATTGTGGA AATCCTCAGG ATTTCTTTTG CAAGCAATGG AGCTGCGTAA 300
CTTCTAATGA TGGGAATTGG AAATGGCCAG TCTCTCAGCA AGACAGAGTA 350
AGTTACTCTT TTGTTAACAA TCCTACCAGT TATAATCAAT TTAATTATGG 400
CCATGGGAGA TGGAAAGATT GGCAACAGCG GGTACAAAAA GATGTACGAA 450
ATAAGCAAAT AAGCTGTCAT TCGTTAGA
```

FIGURE 6 Comparison of the sequences derived from pig 11619

```
11619-1.DNA    1 ATGCATCCCA CGTTAAGCCG GCGCCACCTC CCGATTCGGG GTGGAAAGCC    50
11619-2.DNA    1 ATGCATCCCA CGTTAAGCCG GCGCCACCTC CCGATTCGGG GTGGAAAGCC    50
11619-3.DNA    1 ATGCATCCCA CGTTAAGCCG GCGCCACCTC CCGATTCGGG GTGGAAAGCC    50
11619-4.DNA    1 ---------- ---------- ---------- ---------- ----------    50
11619-5.DNA    1 ---------- ---------- ---------- ---------- ----------    50
11619-6.DNA    1 ---------- ---------- ---------- ---------- ----------    50
11619-7.DNA    1 ---------- ---------- ---------- ---------- ----------    50
11619-8.DNA    1 ---------- ---------- ---------- ---------- ----------    50
11619-9.DNA    1 ---------- ---------- ---------- ---------- ----------    50

11619-1.DNA   51 GAAAAGACTG AAAATCCCCT TAAGCTTCGC CTCCATCGCG TGGTTCCTTA   100
11619-2.DNA   51 GAAAAGACTG AAAATCCCCT TAAGCTTCGC CTCCATCGCG TGGTTCCTTA   100
11619-3.DNA   51 GAAAAGACTG AAAATCCCCT TAAGCTTCGC CTCCATCGCG TGGTTCCTTA   100
11619-4.DNA   51 ---------- ---------- ---------- ---------- ----------   100
11619-5.DNA   51 ---------- ---------- ---------- ---------- ----------   100
11619-6.DNA   51 ---------- ---------- ---------- ---------- ----------   100
11619-7.DNA   51 ---------- ---------- ---------- ---------- ----------   100
11619-8.DNA   51 ---------- ---------- ---------- ---------- ----------   100
11619-9.DNA   51 ---------- ---------- ---------- ---------- ----------   100

11619-1.DNA  101 CTCTGTCAAT AACTCCTCAA GTTAATGGTA AACGCCTTGT GGACAGCCCG   150
11619-2.DNA  101 CTCTGTCAAT AACTCCTCAA GTTAATGGTA AACGCCTTGT GGACAGCCCG   150
11619-3.DNA  101 CTCTGTCAAT AACTCCTCAA GTTAATGGTA AACGCCTTGT GGACAGCCCG   150
11619-4.DNA  101 ---------- ---------- ---------- ---------- -GACAGCCCG   150
11619-5.DNA  101 ---------- ---------- -TTAATGGTA AACGCCTTGT GGACAGCCCG   150
11619-6.DNA  101 ---------- ---------- -TTAATGGTA AACGCCTTGT GGACAGCCCG   150
11619-7.DNA  101 ---------- ---------- ---------- ---------- -GACAGCCCG   150
11619-8.DNA  101 ---------- ---------- -TTAATGGTA AACGCCTTGT GGACAGCCCG   150
11619-9.DNA  101 ---------- ---------- -TTAATGGTA TGCGCCTTGT GGACTGCCCG   150

11619-1.DNA  151 AACTCCCATA AACCCTTATC TCTCACCTGG TTACTTACTG ACTCCGGTAC   200
11619-2.DNA  151 AACTCCCATA AACCCTTATC TCTCACCTGG TTACTTACTG ACTCCGGTAC   200
11619-3.DNA  151 AACTCCCATA AACCCTTATC TCTCACCTGG TTACTTACTG ACTCCGGTAC   200
11619-4.DNA  151 AACTCCCATA AACCCTCATC TCTCACCTGG TTACTTACTG ACTCCGGTAC   200
11619-5.DNA  151 AACTCCCATA AACCCTTATC TCTCACCTGG TTACTTACTG ACTCCGGTAC   200
11619-6.DNA  151 AACTCCCATA AACCCTTATC TCTCACCTGG TTACTTACTG ACTCCGGTAC   200
11619-7.DNA  151 AACTCCCATA AACCCTTATC TCTCACCTGG TTACTTACTG ACTCCGGTAC   200
11619-8.DNA  151 AACTCCCATA AACCCTTATC TCTCACCTGG TTACTTACTG ACTCCGGTAC   200
11619-9.DNA  151 AACTCCCATA AACCCTTATC TCTCACCTGG TTACTTACTG ACTCCGGTAC   200

11619-1.DNA  201 AGGTATTAAT ATTAACAGCA CTCAAGGGGA GGCTCCCTTG GGGACCTGGT   250
11619-2.DNA  201 AGGTATTAAT ATTAACAGCA CTCAAGGGGA GGCTCCCTTG GGGACCTGGT   250
11619-3.DNA  201 AGGTATTAAT ATTAACAGCA CTCAAGGGGA GGCTCCCTTG GGGACCTGGT   250
11619-4.DNA  201 AGGTATTAAT ATTAACAGCA CTCAAGGGGA GGCTCCCTTG GGGACCTGGT   250
11619-5.DNA  201 AGGTATTAAT ATTAACAGCA CTCAAGGGGA GGCTCCCTTG GGGACCTGGT   250
11619-6.DNA  201 AGGTATTAAT ATTAACAGCA CTCAAGGGGA GGCTCCCTTG GGGACCTGGT   250
11619-7.DNA  201 AGGTATTAAT ATTAACAGCA CTCAAGGGGA GGCTCCCTTG GGGACCTGGT   250
11619-8.DNA  201 AGGTATTAAT ATTAACAGCA CTCAAGAGGA GGCTCCCTTG GGGACCTGGT   250
11619-9.DNA  201 AGGTATTAAT ATTAACATCA CTCAAGGGGA GGCTCCCTTG GGGACCTGGT   250

11619-1.DNA  251 GGCCTGAATT ATATGTCTGC CTTCGATCAG TAATCCCTGG TCTCAATGAC   300
11619-2.DNA  251 GGCCTGAATT ATATGTCTGC CTTCGATCAG TAATCCCTGG CCTCAATGAC   300
11619-3.DNA  251 GGCCTGAATT ATATGTCTGC CTTCGATCAG TAATCCCTGG TCTCAATGAC   300
11619-4.DNA  251 GGCCTGAATT ATATGTCTGC CTTCGATCAG TAATCCCTGG TCTCAATGAC   300
11619-5.DNA  251 GGCCTGAATT ATATGTCTGC CTTCGATCAG TAATCCCTGG TCTCAATGAC   300
11619-6.DNA  251 GGCCTGAATT ATATGTCTGC CTTCGATCAG TAATCCCTGG TCTCAATGAC   300
11619-7.DNA  251 GGCCTGAATT ATATGTCTGC CTTCGATCAG TAATCCCTGG TCTCAATGAC   300
11619-8.DNA  251 GGCCTGAATT ATATGTCTGC CTTCGATCAG TAATCCCTGG TCTCAATGAC   300
11619-9.DNA  251 GGCCTGAATT ATATGTCTGC CTTCGATCAG TAATCCCTGG TCTCAATGAC   300

11619-1.DNA  301 CAGGCCACAC CCCCGATGT ACTCCGTGCT TACGGGTTTT ACGTTTGCCC    350
11619-2.DNA  301 CAGGCCACAC CCCCGATGT ACTCCGTGCT TACGGGTTTT ACGTTTGCCC    350
11619-3.DNA  301 CAGGCCACAC CCCCGATGT ACTCCGTGCT TACGGGTTTT ACGTTTGCCC    350
11619-4.DNA  301 CAGGCCACAC CCCCGATGT ACTCCGTGCT TACGGGTTTT ACGTTTGCCC    350
11619-5.DNA  301 CAGGCCACAC CCCCGATGT ACTCCGTGCT TACGGGTTTT ACGTTTGCCC    350
11619-6.DNA  301 CAGGCCACAC CCCCGATGT ACTCCGTGCT TACGGGTTTT ACGTTTGCCC    350
11619-7.DNA  301 CAGGCCACAC CCCCGATGT ACTCCGTGCT TACGGGTTTT ACGTTTGCCC    350
11619-8.DNA  301 CAGGCCACAC CCCCGATGT ACTCCGTGCT TACGGGTTTT ACGTTTGCCC    350
11619-9.DNA  301 CAGGCCACAC CCCCGATGT ACTCCGTGCT TACGGGTTTT ACGTTTGCCC    350
```

Figure 6 (cont'd)

```
11619-1.DNA    351 AGGACCCCCA AATAATGAAG AATATTGTGG AAATCCTCAG GATTTCTTTT    400
11619-2.DNA    351 AGGACCCCCA AATAATGAAG AATATTGTGG AAATCCTCAG GATTTCTTTT    400
11619-3.DNA    351 AGGACCCCCA AATAATGAAG AATATTGTGG AAATCCTCAG GATTTCTTTT    400
11619-4.DNA    351 AGGACCCCCA AATAATGAAG AATATTGTGG AAATCCTCAG GATTTCTTTT    400
11619-5.DNA    351 AGGACCCCCA AATAATGAAG AATATTGTGG AAATCCTCAG GATTTCTTTT    400
11619-6.DNA    351 AGGACCCCCA AATAATGAAG AATATTGTGG AAATCCTCAG GATTTCTTTT    400
11619-7.DNA    351 AGGACCCCCA AATAATGAAG AATATTGTGG AAATCCTCAG GATTTCTTTT    400
11619-8.DNA    351 AGGACCCCCA AATAATGAAG AATATTGTGG AAATCCTCAG GATTTCTTTT    400
11619-9.DNA    351 AGGACCCCCA AATAATGAAG AATATTGTGG AAATCCTCAG GATTTCTTTT    400

11619-1.DNA    401 GCAAGCAATG GAGCTGCGTA ACTTCTAATG ATGGGAATTG GAAATGGCCA    450
11619-2.DNA    401 GCAAGCAATG GAGCTGCGTA ACTTCTAATG ATGGGAATTG GAAATGGCCA    450
11619-3.DNA    401 GCAAGCAATG GAGCTGCGTA ACTTCTAATG ATGGGAATTG GAAATGGCCA    450
11619-4.DNA    401 GCAAGCAATG GAGCTGCGTA ACTTCTAATG ATGGGAATTG GAAATGGCCA    450
11619-5.DNA    401 GCAGGCAATG GAGCTGCGTA ACTTCTAATG ATGGAAATTG GAAATGGCCA    450
11619-6.DNA    401 GCAAGCAATG GAGCTGCGTA ACTTCTAATG ATGGGAATTG GAAATGGCCA    450
11619-7.DNA    401 GCAAGCAATG GAGCTGCGTA ACTTCTAATG ATGGGAATTG GAAATGGCCA    450
11619-8.DNA    401 GCAAGCAATG GAGCTGCGTA ACTTCTAATG ATGGGAATTG GAAATGGCCA    450
11619-9.DNA    401 GCAAGCAATG GAGCTGCGTA ACTTCTAATG ATGGGAATTG GAAATGGCCA    450

11619-1.DNA    451 GTCTCTCAGC AAGACAGAGT AAGTTACTCT TTTGTTAACA ATCCTACCAG    500
11619-2.DNA    451 GTCTCTCAGC AAGACAGAGT AAGTTACTCT TTTGTTAACA ATCCTACCAG    500
11619-3.DNA    451 GTCTCTCAGC AAGACAGAGT AAGTTACTCT TTTGTTAACA ATCCTACCAG    500
11619-4.DNA    451 GTCTCTCAGC AAGACAGAGT AAGTTACTCT TTTGTTAACA ATCCTACCTA    500
11619-5.DNA    451 GTCTCTCAGC AAGACAGAGT AAGTTACTCT TTTGTTAACA ATCCTACCAG    500
11619-6.DNA    451 GTCTCTCAGC AAGACAGAGT AAGTTACTCT TTTGTTAACA ATCCTACCAG    500
11619-7.DNA    451 GTCTCTCAGC AAGACAGAGT AAGTTACTCT TTTGTTAACA ATCCTACCAG    500
11619-8.DNA    451 GTCTCTCAGC AAGACAGAGT AAGTTACTCT TTTGTTAACA ATCCTACCAG    500
11619-9.DNA    451 GTCTCTCAGC AAGACAGAGT AAGTTACTCT TTTGTTAACA ATCCTACCAG    500

11619-1.DNA    501 TTATAATCAA TTTAATTATG GCCATGGGAG ATGGAAAGAT TGGCAACAGC    550
11619-2.DNA    501 TTATAATCAA TTTAATTATG GCCATGGGAG ATGGAAAGAT TGGCAACAGC    550
11619-3.DNA    501 TTATAATCAA TTTAATTATG GCCATGGGAG ATGGAAAGAT TGGCAACAGC    550
11619-4.DNA    501 TAATAATCAA TTTAATTATG GCCATGGGAG ATGGAAAGAT TGGCAACAGC    550
11619-5.DNA    501 TTATAATCAA TTTAATTATG GCCATGGGAG ATGGAAAGAT TGGCAACAGC    550
11619-6.DNA    501 TTATAATCAA TTTAATTATG GCCATGGGAG ATGGAAAGAT TGGCAACAGC    550
11619-7.DNA    501 TTATAATCAA TTTAATTATG GCCATGGGAG ATGGAAAGAT TGGCAACAGC    550
11619-8.DNA    501 TTATAATCAA TTTAATTATG GCCATGGGAG ATGGAAAGAT TGGCAACAGC    550
11619-9.DNA    501 TTATAATCAA TTTAATTATG GCCATGGGAG ATGGAAAGAT TGGCAACAGC    550

11619-1.DNA    551 GGGTACAAAA AGATGTACGA AATAAGCAAA TAAGCTGTCA TTCGTTAGA.    600
11619-2.DNA    551 GGGTACAAAA AGATGTACGA AATAAGCAAA TAAGCTGTCA TTCGTTAGA.    600
11619-3.DNA    551 GGGTACAAAA AGATGTACGA AATAAGCAAA TAAGCTGTCA TTCGTTAGA.    600
11619-4.DNA    551 GGGTACAAAA AGATGTACGA AATAAGCAAA TAAGCTGTCA TTCGTTAGA.    600
11619-5.DNA    551 GGGTACAAAA AGATGTACGA AATAAGCAAA TAAGCTGTCA TTCGTTAGA.    600
11619-6.DNA    551 GGGTACAAAA AGATGTACGA AATAAGCAAA TAAGCTGTCA TTCGTTAGA.    600
11619-7 DNA    551 GGGTACAAAA AGATGTACGA AATAAGCAAA TAAGCTGTCA TTCGTTAGA.    600
11619-8.DNA    551 GGGTACAAAA AGATGTACGA AATAAGCAAA TAAGCTGTCA TTCGTTAGA.    600
11619-9.DNA    551 GGGTACAAAA AGATGTACGA AATAAGCAAA TAAGCTGTCA TTCGTTAGA.    600
```

SWINE DEFECTIVE FOR TRANSMISSION OF PORCINE ENDOGENOUS RETROVIRUS AND USES THEREOF

This application claims the priority of U.S. Provisional Application Ser. No. 60/243,695, filed Oct. 27, 2000, U.S. Provisional Application Ser. No. 60/182,965, filed Feb. 16, 2000, and U.S. Provisional Application Ser. No. 60/177,003, filed Jan. 19, 2000, the disclosures of which are hereby incorporated by reference in their entirety.

FIELD OF THE INVENTION

The present invention is directed to inbred swine free of pig endogenous retrovirus (PERV) sequences that are capable of capable of contributing toward viruses infecting human cells and to methods of xenotransplantation of organs from such swine into humans and to methods of screening such swine at high stringency to insure their freedom from human tropic endogenous retrovirus components otherwise infectious to humans as well as methods for the production of such swine.

BACKGROUND OF THE INVENTION

Organ transplantation is the established treatment for end-stage organ disease. However, there exists a worldwide shortage of organs available for transplantation. In the USA alone, there are currently approximately 60,000 people waiting for organ transplants and 4000 die every year before a transplant can be performed [1] with the waiting list artificially constrained in size due to the limited type and number of donor organs available. Many additional patients that could benefit from organ transplantation are not listed. Xenotransplantation, the use of animal organs and cells for transplantation into humans, has the potential to alleviate this shortage [2]. Although some consideration has been given to the use of non-human primates as donors, swine are now accepted as the animal of choice for xenotransplantation due to a number of practical, financial, and ethical reasons [2].

The present invention solves problems of xenotransplantation by providing a herd of swine, preferably miniature swine, and preferably inbred at the MHC (Major Histocompatibility Complex) locus, for xenotransplantation. In accordance with the invention, miniature swine were chosen for use herein because they exhibit several attractive characteristics. Like their domestic counterparts, miniature swine reach sexual maturity at an age of 4–5 months and give birth to multiple offspring (3–10 per litter). In addition they have an estrous cycle every 3 weeks, permitting breeding throughout the year. Miniature swine reach an adult size of 200–300 pounds (a size comparable to adult humans) in contrast to domestic swine that attain weights of over 1000 pounds. This difference is important in the programmed growth of a transplanted porcine organ. Furthermore, the animals developed herein have been housed under defined conditions and have an extensive medical history associated with them.

Although xenotransplantation clearly has the potential to alleviate much suffering, certain safety concerns are associated with the procedure [3,4]. These concerns can be divided into infectious risk to the patient, and particularly with xenotransplantation the risk to contacts of the recipients. The most serious concern is the possibility of transmission of microorganisms from the xenograft to the recipient and the subsequent emergence of a new human infection and possibly disease. A major reason that pigs are considered the donor animal of choice in preference to non-human primates is due to the reduced microbiological burden that they carry. Risk of transmission of microorganisms is not unique to xenotransplantation. Many cases have been documented of transmission of organisms causing disease during allotransplantation procedures [5].

Cross-species infection (zoonosis), in comparison to transmissions confined within a species, is of particular concern because the behavior of an organism once it crosses the species barrier cannot be predicted by its pathogenicity in its natural host. Organisms benign in their natural host can cause significant morbidity in a zoonotic scenario. This is exemplified by the potentially fatal infections of humans with the Nipah virus of pigs, herpes B virus of primates and hantavirus of rodents [6–8]. Secondly, the consequences of transmission of an organism might not stop solely with the xenograft recipient. The possibility exists that once contracted by the xenograft recipient, the organism may be transmissible to contacts of the recipient. Thus the control and monitoring of recurrent infection during xenotransplantation procedures is viewed as an important public health issue [2]. In addition, although it may be possible to detect an infection of the recipient by a microorganism quickly and before manifestations of disease become apparent, effective treatments may not have been developed because in almost all cases no previous infections by this organism will have been documented. As a consequence, the prognosis of infection by zoonotic microorganisms transmissible through xenotransplantation are essentially unknown and thus the organisms specified for removal include all organisms known to produce disease in either man or pig.

The microorganisms that could be transferred along with the organ vary in their potential to establish an infection in the recipient and therefore their importance to xenotransplantation. Raising animals under germfree methodologies such as described in Ratcliffe and Fodham (1987) *Laboratory Animals* 21: 53–59 facilitates removal and prevention of the reoccurrence in the herd of many of the organisms considered a potential risk to xenotransplantation. The greatest risk of infection is probably with those organisms that have an ability to be transferred as an asymptomatic latent entity within the organ. These problematic characteristics have made endogenous retroviruses (ERV) and herpesviruses the focus of attention by regulatory agencies and the production of animals clear of such organisms a priority. In accordance with the present invention, such problems are wholly, or, at least, partially, solved by the production of certain animals within a herd (such as the miniature swine used herein) with a unique advantage over other breeds of pig with respect to endogenous microorganisms.

Endogenous retroviruses (ERVs) have been identified as a constituent of the normal DNA of every vertebrate species tested including pigs and humans. A unique attribute of the normal retrovirus lifecycle is the stable integration of genetic material into the host cell chromosomal DNA. Where the host cell is a germ-line cell, the viral nucleic acid material (or provirus) will subsequently be inherited by all offspring in a manner typical of any other Mendelian gene. Consequently, if the presence of a particular provirus in the DNA of a germ-line cell places the offspring at a selective disadvantage it would not be expected to survive over evolutionary time periods and this ERV is not expected in the ongoing gene pool. Thus, the ERV present in the germ-line of animals today tend not to be pathogenic for their own species. Individual ERV loci also tend to be replication defective due to mutations present in their genome. However, the potential exists for individual defective loci to interact by complementation and recombination to form infectious virus. The lack of pathogenicity of ERV for their normal host species leaves no room for complacency because the very same viruses can change their pathogenicity when interspecies transmission occurs. For example, Gibbon Ape Leukemia Virus is thought to have evolved following infection of gibbons with a nonpathogenic endogenous virus of mice [9]. It now spreads in captive gibbons causing lymphoid and myeloid malignancies. Furthermore, tumorogenic properties due to the activities of ERV have been observed in non-human primates undergoing retroviral gene therapy treatments [10].

Pig endogenous retroviruses (PERV) represent a unique and possibly the most important safety concern for xenotransplantation. Unlike other infectious organisms that a pig may carry, these viruses are not transmitted between animals as an infectious agent but rather are inherited by all animals as part of their germ-line DNA. The viruses are present in all breeds of swine and form part of the normal DNA present in every cell. Approximately 50 copies of the virus are present in every cell, and as such cannot be completely removed by conventional breeding techniques. As a consequence, these DNA sequences are certain to be present in all swine cells used for xenotransplants.

The production of PERV and transmission to human cells has heretofore been studied in vitro in great detail and it has been shown that two families of PERV (PERV-A and PERV-B) can replicate in human and porcine cells [11,12]. A third family (PERV-C) can replicate in porcine cells only [11,12]. The human kidney cell line 293 is clearly the most permissive for PERV replication and has thus been selected for co-culture assays [11]. Retroviruses use cell surface molecules to act as receptors and mediate virus entry. The expression pattern of these cellular receptors indicates that the three families of PERV use independent receptors, not used by other infectious retroviruses [12]. Significantly, some cells that are permissive for virus entry do not support virus replication [11, 12]. PERV production has been examined from pig cell lines and also from primary cell cultures from several pig breeds [13]. All swine cells, with the single exception of the cell line ST-IOWA, appear to produce PERV capable of infecting and replicating in human cells. Breeds of pig tested to date include the NIH minipig, Yucatan, multiple land breeds, and the animals currently being used in clinical trials. In short, the use of a specific-pathogen-free (SPF) breeding program would eliminate most pathogens that might be transmitted during xenotransplantation. However, pathogens such as ERV that are transmitted through the germ-line would not be eliminated and the recent evidence cited above demonstrates that certain PERVs are capable of infecting human cells so that one of the potential risks from the use of pig organs is the transmission of such pathogens.

Studies into PERV are complicated by the predominance of defective copies of the virus, which are very closely related to replication competent copies of the virus. In order for a single locus to encode for replication competent virus, a genomic copy of PERV must contain functional LTR's and open reading frames for gag, pol and env and it is therefore necessary to be able to identify these loci specifically. In addition, RNA from defective loci may once pseudotyped into human cells, recombine with other PERV loci to form replication competent retrovirus (RCR). Sequencing of isolated single genes, although it may identify open reading frames, cannot be extrapolated as inferring competence of a locus for replication.

The regulatory boards governing xenotransplantation trials in both the USA and UK at one point halted clinical trials in reaction to the initial discovery that human cells could be infected by PERV. Since then a number of published reports have presented data indicating that a limited number of patients transiently exposed to relatively small numbers of porcine cells and organs show no evidence of PERV transmission [14–16]. Limited clinical trials have recommenced with the requirement of chronic screening of recipients for PERV infection. The possible lifelong screening currently required clearly places not only a significant monetary cost on the xenotransplantation procedure, but also a practical burden on the patient due to the repeated monitoring procedures. Consequently, use of animals devoid of transmissible PERV as xenograft donors is not only safer but also affords reduced costs of post-transplant screening procedures.

In accordance with the present invention, the inbred herd of swine used herein contains a novel subgroup of animals that does not produce PERV capable of replication in human cells even by recombinantion. Based on the disclosure herein, specific breeding can be performed to eliminate all genetic components that can contribute to form a human-tropic replication competent PERV present in the pigs.

BRIEF SUMMARY OF THE INVENTION

It is an object of the present invention to provide a swine breed, and methods of producing the same, which breed does not produce porcine endogenous retrovirus (PERV) that can infect human cells, thereby having a unique advantage over other swine breeds with respect to its microbiological safety for xenotransplantation.

It is a further object of the present invention to provide a major histocompatibility complex (MHC) inbred swine, preferably miniature swine, as a source of organs for human xenotransplantation devoid of genetic components that can form a RCR, including a successful breeding program for producing such animals in sufficient quantities to serve as a practical source for such a program. In one embodiment, such swine are miniature swine.

It is a still further object of the present invention to provide such animals on a large scale as sources of clinical grade organs, tissues and cells.

It is also an object of the present invention to provide such a breed having a more appropriate size of full grown adults to serve as solid organ donors for humans, plus a long period, as much as 25 years, of medical and quality information on a closed herd of such animals and animals exhibiting immunological tolerance.

It is a further object of the present invention to provide tissues from such miniature swine as a source of stem cells for xenogeneic stem cell and thymic replacement therapy, for example, in treating AIDS cases.

BRIEF DESCRIPTION OF THE DRAWINGS

FIG. 3 shows the nucleotide sequence of different clones derived from peripheral blood mononuclear cells (PBMC) from swine leukocyte antigen (SLA) inbred miniature swine, numbered 12002 with seven (7) different clones being generated (numbered 1 through 7 in panels 3(a) through 3(g), designated 12002-1 (SEQ ID NO: 1), 12002-2 (SEQ ID NO: 2), 12002-3 (SEQ ID NO: 3), 12002-4 (SEQ ID NO: 4), 12002-5 (SEQ ID NO: 5), 12002-6 (SEQ ID NO: 6), and 12002-7 (SEQ ID NO: 7), respectively. The preparation of these clones is described in Example 4.

FIG. 4 shows the results of a comparison of the nucleotide sequences of the seven clones generated as per example 4 and with the sequences shown in FIG. 3 designated 12002-1 (SEQ ID NO: 1), 12002-2 (SEQ ID NO: 2), 12002-3 (SEQ ID NO: 3), 12002-4 (SEQ ID NO: 4), 12002-5 (SEQ ID NO: 5), 12002-6 (SEQ ID NO: 6), and 12002-7 (SEQ ID NO: 7). Clone 12002-1 exhibits a single nucleotide difference from the other clones at position 349. While this sequence may reflect another variant of the PERV sequence it is also possible that it is an artifact from the cloning or sequencing procedures.

FIG. 5 shows the nucleotide sequence of different clones derived from peripheral blood mononuclear cells (PBMC) from swine leukocyte antigen (SLA) inbred miniature swine numbered 11619 with nine (9) different clones being generated (numbered 1 through 9 in panels 5(a) through 5(i) designated 11619-1 (SEQ ID NO: 8), 11619-2 (SEQ ID NO: 9), 11619-3 (SEQ ID NO: 10), 11619-4 (SEQ ID NO: 11), 11619-5 (SEQ ID NO: 12), 11619-6 (SEQ ID NO: 13), 11619-7 (SEQ ID NO: 14), 11619-8 (SEQ ID NO: 15), and 11619-9 (SEQ ID NO: 16), respectively. The preparation of these clones is described in Example 4.

FIG. 6 is a comparison of the nucleotide sequences of the seven clones generated as per example 4 and with the sequences shown in FIG. 5. All sequences analyzed are of the PERV-AH2 type. Shown are a number of sequences and their alignments for these clones (designated 11619-1 (SEQ ID NO: 8), 11619-2 (SEQ ID NO: 9), 11619-3 (SEQ ID NO: 10), 11619-4 (SEQ ID NO: 11), 11619-5 (SEQ ID NO: 12), 11619-6 (SEQ ID NO: 13), 11619-7 (SEQ ID NO: 14), 11619-8 (SEQ ID NO: 15), and 11619-9 (SEQ ID NO: 16)) which have been studied in detail from the beginning of the envelope gene to the VRB region.

DETAILED DESCRIPTION OF THE INVENTION

Figure 1:
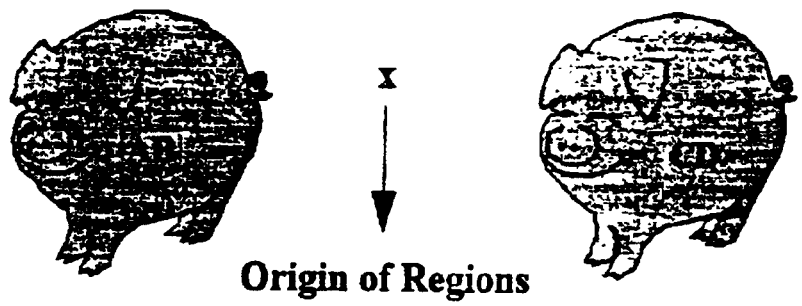
FIG. 1 shows three distinct haplotypes and three recombinants that are maintained within the herd disclosed according to the present invention. The herd of miniature swine are fully inbred at the major histocompatibility complex/swine leukocyte antigen (MHC/SLA) and partially inbred at other loci (currently ~0.82 coefficient of inbreeding).
Figure 1:
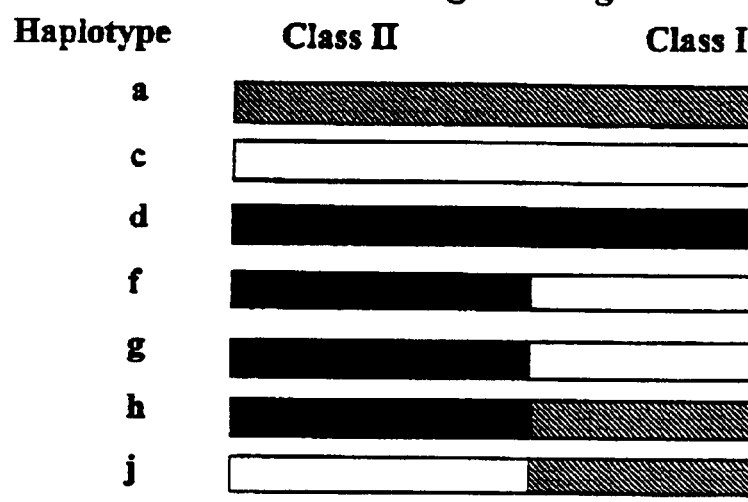

In one aspect, the present invention provides a line of swine with PERVs that, if present at all, are non-infectious to human cells as measured by high stringency in vitro assays disclosed herein. Such animals are thus a valuable source of organs, tissues and cells for xenotransplantation.

As disclosed herein, in order to identify human-tropic viruses, co-culture with human (e.g. 293 cells) is used to select for replication competence. The 293-cell line was used herein because it is the most susceptible cell line for PERV replication identified to date. In accordance with the present invention other human lines may also be used if appropriate and use herein of the 293-cell line is in no way considered limiting of the present invention.

After selecting for replication competent virus, long PCR products (LTR-to-LTR) are generated and cloned. Sequence analysis of these products allows identification of loci that can interact to form a virus that can productively replicate in human cells. This virus may be formed by the product of a single locus or may be a recombinant formed from the products of two or more loci. Using specific probes for these loci as disclosed herein, animals are screened for the presence of particular loci and, thus, critical components of the human tropic PERV. Based on these data, a breeding program is established that rapidly eliminates all the genetic components contributing toward replication competent PERV.

Thus, the present invention relates to a process for xenotransplantation comprising introducing into a human patient in need thereof an organ, tissue or cells derived from a swine free of loci that can form infectious human-tropic PERV, preferably wherein the swine is a miniature swine, most preferably characterized by the DD haplotype. In a further embodiment of the present invention, said swine may contain PERV but if present the latter are not able to form a virus that is infectious to human cells.

Such methods find particular use in the treatment and/or prevention of diseases, especially in human patients, wherein said diseases are the result of poorly functioning organs or tissues, or where such diseases result from inadequate numbers of cells that perform vital physiological functions. In this regard, the introduction into such a patient of a sample of cells derived from a donor organism, such as a swine of the present invention, can prove therapeutically effective in alleviating the disease caused by lack of such cells, or caused by an inadequate number of such cells. Thus, introduction of such cells can not only alleviate a disease condition but also provide additional cells to improve the health of an otherwise healthy patient. While such cells can be derived from any organ, tissue or cells of the miniature swine donor, a preferred embodiment uses stem cells for such treatment.

Thus, in another aspect, the present invention relates to a process for preventing a disease in a human patient comprising introducing into a human patient at risk of said disease an organ, tissue or cells derived from a miniature swine of the present invention without fear that an endogenous retrovirus, especially a pig endogenous retrovirus, will be transmitted as a result of the transplantation process. In a preferred embodiment, said swine is a miniature swine, most preferably characterized by the DD haplotype.

The present invention further relates to a process for treating a disease in a human patient afflicted with said disease comprising introducing into a human patient in need thereof the organ, tissue or cells derived from the swine disclosed herein, especially where such swine is a miniature swine, most especially of the DD haplotype. In accordance with the present invention, such swine may be swine that possess PERV that are non-infectious to human cells. In keeping with the invention disclosed herein, the cells of such swine may even contain componenets of PERV, capable of infecting other swine cells or cells of non-human animals, but such cells do not contain PERV components capable of infecting human cells when in contact with such cells. Thus, use of such organs, tissues, or cells for transplantation into, or otherwise introducing such organs, tissues, or cells into, human recipients does not result in infection of the cells of such human recipient with any ERV derived from the transplanted organs, tissues, or cells.

In accordance with the present invention, the swine, such as miniature swine, useful in treating such diseases are preferably of the DD haplotype (as defined herein). The transplanted organs or tissues useful in practicing the xenotransplantation methods of the present invention include a therapeutically effective amount of a sample of cells, commonly derived from such organs or tissues. In a preferred embodiment, the cells are stem cells.

In another aspect, the present invention relates to a process for screening animals for endogenous retroviral (ERV) DNA comprising the steps of:

(a) obtaining a sample of peripheral blood mononuclear cells (PBMC) from an animal to be tested and stimulating ERV expression in said cells by contacting said cells with a stimulatory amount of an ERV stimulating agent;

(b) contacting said stimulated cells of step (a) with a sample of uninfected indicator cells and co-culturing said cells so as to permit infection;

(c) repeating the procedure of steps (a) and (b) on separate aliquots of cells to form a second co-culture;

(d) combining the co-cultures produced by steps (b) and (c); and (e) measuring reverse transcriptase activity in the cells of step (d)

whereby the presence of said reverse transcriptase activity is indicative of the presence of ERV virus particles.

During the above screening procedure pigs might be identified that do not transmit PERV. As such these animals have been specifically identified and should thus be used to form the basis of the herd free of human-tropic PERV.

As demonstrated in the examples provided herein, such screening can be conveniently performed by the Product Enhanced Reverse Transcriptase (PERT) assay, although other assays are available. Also in accordance with the present invention, the animal so screened is commonly a swine, especially a miniature swine, most especially a miniature swine of the DD haplotype, and the ERV is a PERV.

In specific embodiments, indicator cells are human cells but may also be cells derived from other species, such as swine, especially miniature swine. In addition, the ERV stimulatory agents may be phytohemagglutinin (PHA) and the phorbol ester: phorbol 1,2 myristate 1,3 acetate (PMA). Further specific embodiments include those where step (c) is carried out 24 hours after step (b) and wherein step (d) is carried out at least about 7 days after step (b). In another specific embodiment, the cells present in the co-culture are in a ratio of about 5:1 for PBMC:indicator cells, especially where the number of indicator cells is about $2 \times 10^5$ and the number of PBMC is about $10^6$.

In a specific embodiment, a sufficient period of time for stimulation is at least about 3 days but may be longer or shorter depending on the other conditions utilized for the screening process as well as on the needs and inclinations of the researcher and/or clinician.

In a further embodiment, the present invention relates to an inbred swine, such as a miniature swine, preferably of the DD haplotype, wherein said miniature swine is inbred so as to remove PERV gene sequences infectious for humans from the genome thereof. In a preferred embodiment, such PERV sequences are not present at all while in other embodiments such PERV may be present but are non-infectious to humans and human cells.

In general, analysis of PERV transmission in vitro follows a basic protocol. Briefly, blood is taken from test animals using standard phlebotomy techniques and peripheral blood mononuclear cells (PBMC) isolated by FICOLL™ separation using standard technology. PERV expression in the cells is induced by stimulation in RPMI medium containing 20% fetal bovine serum (FBS), phytohemaglutinin (PHA, 2 µg/ml) and the phorbol ester PMA (10 ng/ml). Following a 4–5 days stimulation period, uninfected human (293) or porcine (ST-IOWA) cells are added to the porcine PBMC (ST-IOWA cells are the only porcine cell line identified that do not produce infectious PERV particles). After waiting at least 48 hours the cells are maintained in a culture medium consisting of Dulbecco's medium supplemented with 10% FBS. In order for viral replication to become established and increase to detectable levels, the cultures may require maintenance for up to 60 days before a definitive result is obtained. Transmission of virus is determined by the presence of reverse transcriptase (RT) activity in the supernatant of the cultures using either a product-enhanced RT (PERT) assay (18) or standard radionucleotide RT assay or ELISA. At early co-culture time points porcine PBMC coexist with the human and porcine target cells. Consequently PERV transmission can only be assumed following a positive reverse transcriptase result in the absence of residual porcine PBMC.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which those procedures are described. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

In general, many of the techniques utilized by the methods disclosed herein are to be found in well known molecular biology references and publications, including, but not limited to, such reference works as Sambrook, et al., Molecular Cloning: A Laboratory Manual, Second Edition, Cold Spring Harbor, N.Y., (1989), Wu et al, Methods in Gene Biotechnology (CRC Press, New York, N.Y., 1997), and Recombinant Gene Expression Protocols, in Methods in Molecular Biology, Vol. 62, (Tuan, ed., Humana Press, Totowa, N.J., 1997), the disclosures of which are hereby incorporated by reference.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

Co-Culture Experiments Showing that D/D Miniature Swine do not Produce Human Tropic PERV In this assay the following co-culture conditions were performed. It should be noted that this assay varied in some important details from the established methodologies previously described in the literature [13]. Following purification from fresh blood from D/D haplotype miniature swine, $5 \times 10^6$ lymphocytes were stimulated with PHA and PMA (with or without pretreatment by 2 Gy irradiation) and co-cultured directly with either $1 \times 10^6$ human or porcine cells. The porcine kidney cell line PK15 was used as a positive control for the co-culture assays because these cells produce two families of PERV that can replicate in human cells [11,12]. Control cultures of human and porcine target cells alone were also initiated to ensure absence of retroviral contamination and that the PERV detected originated from the swine PBMC and not from the porcine target cells themselves. Shown in Table 1 are the RT results performed 39 days after co-culture of the porcine and human cells.

TABLE 1

Co-culture results for human and porcine cells.

| PORCINE PRODUCER CELLS | TARGET CELL LINE | RT ASSAY CPM (RADIO-NUCLEOTIDE) | RT ASSAY (PERT) |
|---|---|---|---|
| Non-irradiated PBMC | Human (293) | 560 | Negative |
| Irradiated PBMC | Human (293) | 514 | Negative |
| Non-irradiated PBMC | Porcine (ST-IOWA) | 20,700 | ++ |
| Irradiated PBMC | Porcine (ST-IOWA) | 20,400 | ++ |
| Irradiated PK 15 | Human (293) | 34,000 | +++ |
| None | Human (293) | 327 | negative |
| None | Porcine (ST-IOWA) | 1260 | negative |

The results indicate that although D/D miniature swine PBMC can produce PERV infectious for pig cells, no virus was produced that could replicate in human (293) cells. The 293 cultures were fully permissive for PERV replication as indicated by the PK15 cell control.

EXAMPLE 2

Increased Stringency in Coculture Experiments Confirms that D/D Miniature Swine do not Produce Human Tropic PERV As a more stringent analysis of PERV transmission to human cells the following stimulation protocol was adopted. PBMCs were isolated from fresh blood from A/A and D/D haplotype animals, resuspended at $10^6$ cells per ml in RPMI medium and stimulated with PHA and PMA. At three days post stimulation, $2\times10^6$ uninfected human or porcine indicator cells were added to $10^7$ PBMC. This co-culture procedure was repeated on further aliquots of cells 24 hours later to maximize the period during which PERV may transmit from the PBMC to indicator cells. The two separate co-cultures were then pooled on day 7 and maintained in culture. RT production was assessed by PERT assay.

Significantly, the D/D haplotype cells from another individual animal again did not produce virus that transmitted to human cells. Under these increased stringency conditions, both A/A as well as D/D haplotypes produced PERV that infected ST-IOWA cells. This shows that the lack of ecotropic virus production observed in the ST-IOWA co-culture above probably represents a quantitative difference in ecotropic virus production between the D/D and other haplotype animals.

of PHA and PMA to induce PERV expression [13]. Effective stimulation of the cells is necessary to ensure maximum virus production and sensitivity of the co-culture assays. It is important therefore to ensure that the D/D haplotype cells are being stimulated efficiently, as the lack of virus production observed with these cells could be due to reduced stimulation rather than a difference in the spectrum of infectious PERV present in the cell genome. To address these concerns, PBMCs are isolated from the blood of all haplotypes of miniature swine blood using Ficoll separation. Cultures using standard numbers of cells are established in RPMI supplemented with 10% FBS. The cells are then stimulated with varying concentrations of PHA and PMA, and the efficiency of the stimulation measured at time-points up to 7 days post-stimulation and tritiated thymidine uptake used to assess cell proliferation. The efficiency of PMA activation is assessed by the effect on PERV RNA expression using northern blotting of cell RNA using DNA probes designed to regions located in the envelope gene that differentiate between the three families of replication competent PERV (PERV-A, -B and -C). Quantitative RT-PCR is performed targeting the same family-specific PERV regions. While it is not possible to specifically test the cells for the RNA of human-tropic PERV, data pertaining to the bulk PERV population provides confidence to our presumption that D/D PBMC can respond in culture to the mitogenic stimuli in a manner comparable to PBMC obtained from animals of other haplotypes of miniature swine and breeds of pigs.

TABLE 2

Results of stringent analysis of PERV transmission to human cells.

| HAPLOTYPE | TARGET CELL TYPE | D + 28 | D + 35 | D + 42 | D + 49 | D + 60 | D + 102 |
|---|---|---|---|---|---|---|---|
| A/A | Porcine (ST-IOWA) | + | + | + | + | + | + |
| D/D | Porcine (ST-IOWA) | + | + | + | + | + | + |
| A/A | Human (293) | + | + | + | + | + | + |
| D/D | Human (293) | − | − | − | − | − | − |

The results presented in Tables 1 and 2 show that the D/D haplotype miniature swine represents a novel and useful animal for use in xenotransplantation procedures. It is therefore a further object of the present invention to provide such animals for xenotransplantation.

Under most circumstances, characterization of the production of a microorganism consists of well-established tests and methodologies. However, investigations into ERV are significantly more complex due to the endogenous nature of the viruses, and also because the infectious copies of the virus represent only a minority of the copies present in the genome. As a consequence, using established standard assay methodologies, results pertaining specifically to the infectious viruses are potentially masked by the behavior of the closely related but defective elements.

Consequently, a still further object of the present invention is to provide the stringent assay procedure disclosed herein.

In developing this or similar assays, a number of considerations are involved and these must be addressed by any successful stringent assay. One such consideration is the possible causes for the lack of human-tropic PERV from D/D haplotype cells. This could be due to the possibility that D/D haplotype miniature swine PBMC fail to respond to mitogenic stimulation such as that used herein. In the assay disclosed herein, the PBMCs are exposed to a combination A second concern regarding the lack of human-tropic virus production from the D/D animal PBMC of the present invention is to identify which PERV exist in swine genomes that can mediate replication in human cells. To date, the spectrum of PERV that infect human cells has never been fully examined and as a consequence it is still not certain how many distinct functional PERV loci exist in the pig genome that are of clinical importance to xenotransplantation.

If this number is low then it might be possible that the lack of virus production observed in cells from the D/D animals is due to the absence of a small number of crucial PERV loci. If the number is high, it is probable that the effect is due to a difference in the activation of PERV transcription, production, or stability of the virus particles produced by the D/D haplotype animals.

To date, the spectrum of PERV that infect human cells has never been fully examined and as a consequence it is still not certain how many distinct functional PERV loci exist in the genome that are of clinical importance to xenotransplantation. It is clear from the results disclosed herein that human-tropic replication competent PERV are present in the A/A haplotype miniature swine. From the literature it is known that PERV can also be isolated from several other pig breeds [17]. Thus the A/A haplotype miniature swine are readily available as controls for which the loci contributing toward replication competent PERV burden can be evaluated. Determination of the loci present in these animals facilitates determination of presence or absence of these viruses in the genome of the D/D miniature swine. However, it should be reiterated that whether the animals in question have PERV is not a limitation of the invention disclosed herein since the animals disclosed according to the present invention are for use as donors in xenotransplantation without danger of infecting the recipient. The present invention makes available such animals for use as donors, provides methods for such transplantation using said animals and discloses a stringent assay for use in demonstrating the utility of such animals for the claimed purpose as well as for the screening or other animals for the presence of PERV that would otherwise put the human recipient at risk of infection.

Such concerns are addressed by using PBMCs from all haplotypes of miniature swine isolated from fresh blood, stimulated with PHA and PMA, and co-cultured with human 293 cells using the increased stringency screening process disclosed herein, which then allows sequential samples of the infected cells to be harvested, genomic DNA prepared, and the spectrum of PERV transferred to the cell examined by DNA PCR. In accordance with this aspect of the novel stringent screening procedure disclosed herein, there is provided a PCR-based PERV-typing system for amplifying effectively full-length PERV genomes from cellular DNA and distinguishing between very closely related loci. Having determined the spectrum of sequences capable of replicating in human cells it is then possible to determine if these sequences are present in the genome of D/D haplotype miniature swine. Their absence then shows a lack of production of human-tropic virus from the cells of the D/D haplotype animals.

Figure 2:
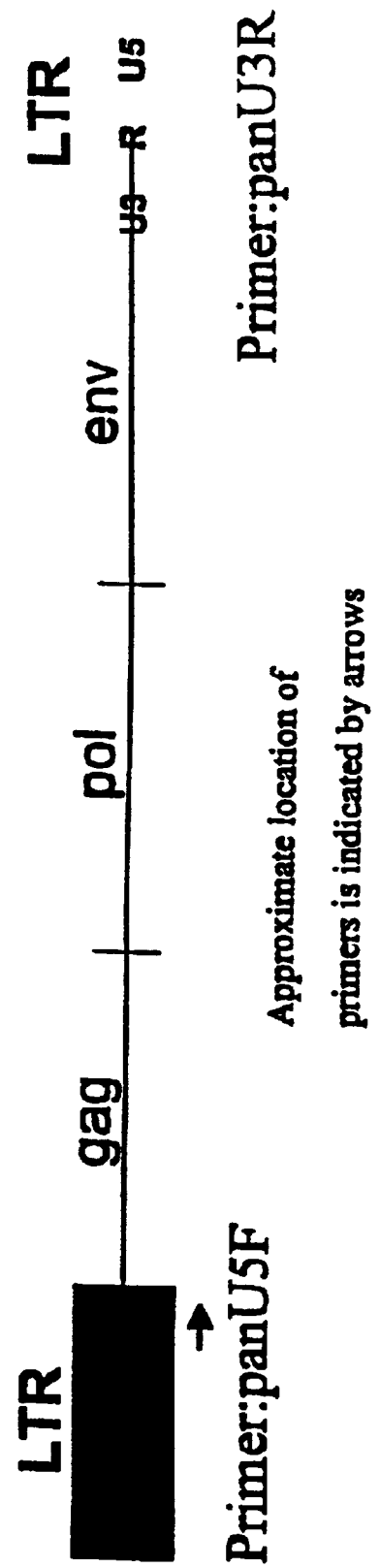
FIG. 2 shows the arrangement of the PERV (Pig Endogenous Retrovirus) genome and the location of the primers used to amplify it.

In accordance with this aspect of the present invention, the PCR primers used in the PERV-typing system are located within conserved sequences in the U5 and U3 regions of the viral LTRs. Thus, the amplicons obtained using these primers will encompass all three major open reading frames as detailed schematically in FIG. 2. It is necessary to amplify near full-length PERV genomes in order to determine which loci contribute toward the formation of infectious virus. Amplification of individual genes would yield effectively uninterpretable results as the ability to distinguish between closely related sequences would be very much impaired, and the linkage of a particular functional gene to other functional genes present within the same locus would not be possible.

The primer sequences used are as follows:

```
PanU5F    GTGTGTCTGGATCTGTTGGTTTC    SEQ ID NO:17
PanU3R    CCACGCAGGGGTAGAGGACT       SEQ ID NO:18
```

PanU5F corresponds to residues 516–538 of Sus scrofa porcine endogenous retrovirus PERV-MSL (Genbank Accession No. gb| AF038600) while PanU3R corresponds to the reverse complement (residues 8067–8048) of the porcine endogenous retrovirus PERV-MSL (Genbank Accession No. gb| AF038600).

After obtaining full length amplicons from genomic DNA by PCR with a long-range (proof-reading) Taq polymerase, they are cloned and analyzed by restriction enzyme digestion using enzymes with either six or four base recognition sequences, or DNA sequencing. Analysis of the restriction fragments obtained facilitates differentiation between very closely related PERV. The use of numerous controls ensures that the number of replication competent PERV is not being overestimated.

A further concern that is also addressed by the novel screening procedure of the present invention is whether the lack of production of human-tropic PERV from D/D animals is a qualitative or a quantitative effect.

Because specific measurement of human-tropic virus without in vitro co-cultivation is not possible at this time, two families of PERV as defined (PERV-A and PERV-B) by their envelope gene sequences have been identified that are replication competent for human cells. As detailed in FIG. 1, three pure MHC haplotypes and four recombinant haplotypes are maintained by selective breeding within the herd. While the results presented in Tables 1 and 2 are derived from the three pure haplotypes of miniature swine (A/A, C/C, and D/D), this is readily expanded, using the disclosure herein, to the analysis of the pure haplotype animals and also the MHC Class I-Class II recombinant animals. All assays for infectious virus are readily performed as in the high stringency assay described herein. Thus, PHA and PMA stimulation of PBMC induces a relatively short period of virus production 4–5 days after initiation of the co-culture [13]. Assays are thus performed herein so as to ensure that the D/D haplotype cells follow this behavior and thus that the human indicator cell line is in direct co-culture with the PBMC during this period.

In addition, standard numbers of fresh PBMC from transmitting miniature swine are isolated and cultured in the presence of PHA and PMA with RT activity measured in the culture supernatants using a product enhanced RT (PERT) assay to follow the kinetics of virus production induced in the cells [19]. In addition to the PERT analysis, RT activity can also measured by a commercial quantitative ELISA based RT assay that has been optimized for PERV detection (Cavidi Tech AB, Sweden).

The present invention also readily permits use of any kind of target cell susceptible to PERV infection. Thus, in accordance with the present invention, alternative human indicator cell lines are available to ensure that the D/D haplotype cells are not producing human-tropic virus that can replicate in human cells other than 293 cells. To date, most co-culture assays have been performed using the 293 cell line as it appears to be the most permissive for human-tropic PERV replication. In accordance with these aspects of the present invention, cell lines permissive for virus entry (i.e. express the PERV envelope receptor molecule) other than 293 are available as the target cell for using the high stringency co-culture methods disclosed herein. Suitable lines include primary human PBMC, and the cell lines HT1080, TE671, and Hale. The HT1080 cell line will be particularly informative as pseudotypes of PERV-C, a virus which is considered to be capable of infecting only porcine cells, is capable of entry into these cells [12].

An additional concern addressed by the high stringency methods disclosed herein is the possibility that cells from the D/D and A/A haplotype animals produce similar titers of virus, but that the D/D derived virus is less infectious due to reduced stability in culture at 37° C. Sucrose gradient fractionation of the virus particles produced by the cells of the D/D and A/A miniature swine indicates whether such particles are stable or not. Here, culture supernatant is collected from the stimulated PBMCs and fractionated according to its density using sucrose gradient centrifugation [11]. The distribution of PERV particles across the sucrose gradient readily allows determination of whether the particles released from the cells are fully mature. The presence of infectious PERV particles from cells of the D/D and A/A haplotypes of miniature swine in gradient fractions (using 293 co-culture) indicates the effect of incubation at 37° C. on the infectious titer of standardized virus preparations.

EXAMPLE 3

Identification of Primers for use in PCR of Near Full-Length PERV Sequences

Primer Design

In accordance with the present invention, PCR primers with capacity to amplify near full-length PERV sequences were designed for the purpose of amplification of all known C-type PERV nucleotide sequences and were aligned using the program GeneWorks. For alignment the following PERV nucleotide sequences were retrieved using Blast searches in Genbank (http://www.ncbi.nlm.nih.gov/BLAST/).

| Virus Designation | Accession Number. |
|---|---|
| PERV-A | AF038601 |
| PERV-B | Y17013 |
| PERV-C | AF038600 |

The LTR regions of PERV-A, -B and -C were aligned. In these LTR regions, nucleotide sequences common to all three proviruses were identified for further analysis. Each nucleotide sequence was then run on the Program Genosys Oligo Calculation in order to determine their suitability as a PCR primer (http://www.genosys.com). The suitability criteria included: a length between 20 and 28 bp, a Tm of about 65° C., a GC content between 45% and 75%, no potential to form a secondary structure, no formation of primer dimers. In addition each primer needs to have a unique binding site on either the 5' or 3' end of the PERV LTRs. Based upon these criteria the following PCR primers were identified:

PCR Protocol

| Step | PCR program temperature (° C.) | PCR program time |
|---|---|---|
| 1 | 94 | 3 min |
| 2 | 94 | 10 sec |
| 3 | 64 | 30 |
| 4 | 68 | 6 min |
| 5 | 68 | 20 min |
| 6 | 6 | Hold |

Steps 2 through 4 were repeated 30 times prior to performing steps 5 and 6. From this analysis four primer pairs were selected for use in the subsequent identification of the human tropic PERVs, namely JWF-1/JWR-5, JWF-2/JWR-5, JWF-3/JWR-5 and JWF-4/JWR-5.

EXAMPLE 4

Characterization of loci that Contribute Toward Human Tropic PERV Present in Individual Pigs This process involved two steps: co-culture of pig cells from individual pigs with human, e.g. 293, cells and subsequent identification of the number of different types of PERV present in the sample following DNA sequence analysis of individual clones.

Peripheral blood mononuclear cells (PBMC) from swine leukocyte antigen (SLA) inbred miniature swine (Transplantation Biology Research Center, Massachusetts General Hospital, Boston, Mass.) numbers 12002 and 11619

TABLE 3

PCR Primers used to Amplify C-Type PERVs

| Name | Forward/Reverse (+/−) | Sequence (5' to 3') | Length | Tm | GC % | Position PERV-A AF038601 | Position PERV-B Y17013 | Position PERV-C AF038600 |
|---|---|---|---|---|---|---|---|---|
| JWF-1 | + | CTAGGAGGATCACAGGCTGC (SEQ ID NO: 19) | 20 | 64 | 60 | 352–371 | 14–33 | 339–358 |
| JWF-2 | + | CCTGGTGGTCTCCTACTGTCG (SEQ ID NO: 20) | 21 | 66 | 62 | 414–434 | 76–96 | 401–421 |
| JWF-3 | + | GTGTGTCTGGATCTGTTGGTTTC (SEQ ID NO: 21) | 23 | 65 | 48 | 529–551 | 191–213 | 516–538 |
| JWF-4 | + | TGCCTGCTTGTGGAAGACG (SEQ ID NO: 22) | 19 | 68 | 59 | 498–516 | 160–178 | 485–503 |
| JWR-5 | − | GCTTTTATGGGGTTCACAACAAA (SEQ ID NO: 23) | 23 | 66 | 39 | 7220–7198 | 7762–7740 | 8021–7999 |
| JWR-6 | − | CCACGCAGGGGTAGAGGACT (SEQ ID NO: 24) | 20 | 67 | 65 | 7266–7247 | 7808–7789 | 8067–8048 |

PCR Optimization

Optimization was performed using DNA from human 293 cells infected with PERV-B. These cells are infected with only one porcine provirus giving the opportunity to optimize the system on known full length PERV DNA. The infected cell line was derived by co-culture with PK-15 porcine kidney cell line.

In order to amplify near full-length retroviral genomes, and to amplify sequences accurately enough for closely related sequences to be differentiated, it is necessary to use DNA polymerases which can amplify long regions of DNA. Examples of such enzymes include TaKaRa DNA polymerase (Intergen Company, Purchase, N.Y.), Clontech Advantage DNA polymerase (Palo Alto, Calif.).

were purified by Ficoll™ gradient separation from freshly drawn blood and stored frozen under liquid nitrogen until analyzed. Using $10^6$ cells per ml, PERV expression in the cells was induced by stimulation in RPMI medium containing 20% fetal bovine serum (FBS), 2 μg/ml phytohemagglutinin (PHA) and 10 ng/ml phorbol 1,2 myristate 1,3 acetate (PMA). At three days post stimulation, approximately $2\times10^6$ uninfected human 293 cells were added to $10^7$ porcine PBMC. This co-culture procedure was repeated on further aliquots of cells 24 hours later in order to maximize the period during which PERV may transmit from the PBMC to the indicator cells. The two separate co-cultures were then pooled at day 7 and maintained in culture. The infection of the cells was determined by the presence of reverse transcriptase (RT) activity in the culture supernatants and can be measured by PERT or commercial ELISAs (Cavidi Tech AB, Uppsala, Sweden).

TABLE 4

PERV transmission using MHC inbred miniature swine

| Animal haplotype | Class II SLA | Class I SLA | Transmission into pig cells | Transmission into human cells |
|---|---|---|---|---|
| A/A | A | A | 4/4 | 1/2 |
| C/C | C | C | 4/4 | 2/2 |
| D/D | D | D | 12/12 | 0/12 |
| H/H | D | A | 3/3 | 2/3 |
| K/K | A | C | 2/4 | 2/4 |
| A/D | A | D | 2/2 | 1/2 |
| C/D | C | D | 1/1 | 1/2 |

Genomic DNA was isolated and PCR products were generated using LTR-to-LTR PCR from cultures showing high levels of RT activity.

PCR products were cloned using the TOPO XL Cloning kit as per the manufacturer's instructions (Invitrogen, Carlsbad, Calif.). Colonies were grown on LB agar plates containing kanamycin (100 ng/µl).

DNA sequencing can be performed over the PERV genome (bounded by the LTR-to-LTR primers used to isolate the virus sequence). However the most informative sequence information is within the highly divergent envelope region. Primers such as those detailed below can be used to determine the complete sequence of the envelope open reading frame. In the experiments performed to date, DNA was prepared from 16 colonies by standard techniques and subjected to sequence analysis in order to determine the number of different types of replication competent PERV present in two samples. The sequencing primer DA185 which corresponds to nucleotides 5561–5585 of Genbank Accession Number AF038600, a region 5' to the initiator methionine codon for the env protein. The use of DA185 enables a sequencing analysis of a portion of PERV env that shows at least 2 distinct point mutations defined as PERV-AH1 and PERV-AH2. Seven sequences have been derived thus far from pig 12002 (see FIGS. 3–4) and nine from pig 11619 (FIGS. 5–6).

PERV 1,2 and 3. The two pigs are mated. From such a mating the potential offspring would have any of the following human tropic PERV combinations:
1,2,3,4
1,2,3
1,2,4
1,2.
The 1,2 animal would be mated with a pig identified to carry 3 and 4 with the resulting possible offspring being:
1,2,3,4
1,2,3
1,2,4
1,3,4
1,3
1,4
1,2
2,3,4
2,3
2,4
3,4
1
2
3
4
None The breeding program would be continued using those animals free from human-tropic PERV.

Thus, the present invention also relates to a process for producing a human-tropic ERV-free animal from parental animals at least one of which is human-tropic ERV-positive, comprising:
(a) mating a male and a female animal of the same species wherein at least of said animals is positive for a human-tropic ERV-locus and thereby producing offspring; and
(b) selecting offspring free of human-tropic ERV.

In a particular aspects, the invention also relates to a process for producing a human-tropic ERV-free animal from parental animals at least one of which is human-tropic ERV-positive, comprising:
(a) mating a male and a female animal of the same species wherein at least one of said animals is positive for a human-tropic ERV-locus and thereby producing offspring;

TABLE 5

| Name | Specificity | Forward/Reverse (+/−) | Sequence (5' to 3') | |
|---|---|---|---|---|
| PERVAF | PERV-A | + | CCT ACC AGT TAT AAT CAA TTT AAT TAT GGC | (SEQ ID NO: 25) |
| PERVAR | PERV-A | − | AGG TTG TAT TGT AAT CAG AGG GG | (SEQ ID NO: 26) |
| JWFPAN1 | PERV-A,B,C | + | CGT GGT TCC TTA CTC TGT CAA TAA CTC | (SEQ ID NO: 27) |
| JWFPAN2 | PERV-A,B,C | + | CTA ATG ATG GGA ATT GGA AAT GG | (SEQ ID NO: 28) |
| JWFPAN4 | PERV-A,B,C | + | GCT TAC CCT TAC TGA GGT TTC TGG | (SEQ ID NO: 29) |
| JWFPAN5 | PERV-A,B,C | + | GGA CTT AGT AAC CTA CAT CGA ATT GTA AC | (SEQ ID NO: 30) |
| JWRENV4 | PERV-A,B,C | − | CCA ACA AGA AGA GGT AGC CTC TG | (SEQ ID NO: 31) |
| JWRENV5 | PERV-A,B,C | − | GGA TCT TCC GTT ACA ATT CGA TGT AG | (SEQ ID NO: 32) |
| DA 185 | PERV-A,B,C | − | TCT CGT ACT TTT TGA CCA CAC CAA CG | (SEQ ID NO: 33) |

EXAMPLE 5

A Breeding Program to Generate Swine Free of PERV that can Infect Human Cells

An example of the breeding program is carried out as follows:

Using methods described in Example 2 a male pig is identified to carry human tropic PERVs arbitarily designated as PERV 1, 2 and 4 (the number of PERVs present can vary but for this Example the pig has three human tropic PERVs). Similarly a female pig is identified to carry human tropic (b) mating a male animal produced in (a) with a female animal produced in (a) wherein at least one of said male and female is positive for a human-tropic ERV-locus and wherein if both are positive for an ERV-locus then said male and female are not each positive for the same human-tropic ERV-locus; and
(c) selecting those offspring that are human-tropic ERV-free.

In a preferred embodiment, said animal is a swine, most preferably a miniature swine, especially a miniature swine of the DD haplotype.

In another preferred embodiment, the present invention relates to a process for producing a human-tropic ERV-free animal from parental animals at least one of which is human-tropic ERV-positive process wherein said ERV is a PERV. Such human-tropic ERV loci are commonly determined using oligonucleotide probes.

In a preferred embodiment of the processes of the present invention, both male and female swine mated in step (a) recited above are human-tropic PERV-positive and wherein the offspring of (a) that are mated in (b) recited above are each human-tropic PERV-positive animals. In a preferred embodiment of such process, said swine are miniature swine, especially miniature swine of the DD haplotype.

In another preferred embodiment of the present invention, the swine mated in (a) recited above are each positive for all but one human-tropic PERV-locus, said male and female so mated are each negative for a different PERV-locus, and the male and female of each mated pair of offspring mated in (b) recited above are each, positive, if at all, for a set of human-tropic PERV-loci with no human-tropic PERV loci in common.

In a specific embodiment of the processes of the invention, step (a) comprises mating pigs carrying PERV 1, 2, 4 and pigs carrying PERV 1, 2, 3 to produce offspring and step (b) comprises mating offspring of (a) carrying PERV 3, 4 with the step (a) 1, 2 positive offspring.

In a highly specific embodiment of such a process, the pigs in step (a) carrying PERV 1, 2, 4 are male pigs and said pigs in step (a) carrying PERV 1, 2, 3 are female pigs. In another highly specific embodiment, the pigs in (b) carrying PERV 3, 4 are male pigs and said pigs in step (b) carrying PERV 1, 2 are female pigs. In a very specific embodiment thereof, the pigs in step (a) carrying PERV 1, 2, 4 are male pigs and the pigs in step (a) carrying PERV 1, 2, 3 are female pigs and wherein said pigs in (b) carrying PERV 3, 4 are male pigs and said pigs in step (b) carrying PERV 1, 2 are female pigs. In a preferred embodiment of this process, said swine is a miniature swine, especially miniature swine of the DD haplotype.

References

1. Critical Data, UNOS. at www.unos.org.
2. Institute of Medicine. Xenotransplantation, science, ethics and public policy. (National Academy Press, Washington D.C., 1996).
3. Stoye J P and Coffin J M. Nature Med, 1:1100 (1995).
4. Allan J S. Nature Medicine, 2:18–20 (1996).
5. Fishman J A and Rubin R H. NEJM, 338:1741–51 (1998).
6. Lim C C, et. al. Singapore Med J, 5:356–8 (1999).
7. Fishman J A. Kidney Int, 51, Supl 58:S41–55 (1997).
8. Mills J N et. al., Emerg Infect Dis, 5:135–42 (1999).
9. Lieber M M et. al., Proc Natl Acad Sci USA, 72:2315–9 (1992).
10. Donahue et. al., J Exp Med, 176:1125–35 (1992).
11. Patience et. al., Nature Med, 3:282–6 (1997).
12. Takeuchi et. al., J Virol, 72:9986–9 (1998).
13. Wilson C A et. al., J Virol, 72:3082–7 (1998).
14. Heneine W et. al., Lancet, 352:695–9 (1998).
15. Patience C et. al., Lancet, 352:699–701 (1998).
16. Paradis K et. al, Science, 285:1236–41 (1999).
17. Martin U et. al., Lancet, 352:692–4 (1998).
18. Silver J et. al., Nucleic Acids Res 21:3593–4 (1994).

What is claimed is:

1. A process for producing a human-tropic PERV-free swine from parental swine at least one of which is human-tropic PERV-positive, comprising:
   (a) mating a male and a female swine of the same species wherein at least one of said swine is positive for a human-tropic PERV-locus whereby said mating produces offspring; and
   (b) screening said offspring for the presence of said human-tropic PERV and selecting offspring free of human-tropic PERV, thereby producing a human-tropic PERV-free swine.

2. A process for producing a human-tropic PERV-free swine from parental swine at least one of which is human-tropic PERV-positive, comprising:
   (a) mating a male and a female swine of the same species wherein at least one of said swine is positive for a human-tropic PERV-locus and thereby producing offspring;
   (b) mating a male swine produced in (a) with a female swine produced in (a) wherein at least one of said male and female is positive for a human-tropic PERV-locus and wherein if both are positive for an PERV-locus then said male and female are not each positive for the same human-tropic PERV-locus; and
   (c) screening said offspring for the presence of said human-tropic PERV and selecting those offspring that are human-tropic PERV-free thereby producing a human-tropic PERV-free swine.

3. The process of claim 2 wherein said human-tropic PERV-free swine is a miniature swine.

4. The process of claim 3 wherein said miniature swine is of the D/D haplotype.

5. The process of claim 2 wherein said human-tropic PERV loci are determined using oligonucleotide probes.

6. The process of claim 2 wherein both male and female swine mated in step (a) are human-tropic PERV-positive and wherein the offspring of (a) that are mated in (b) are each human-tropic PERV-positive swine.

7. The process of claim 2 wherein said human-tropic PERV-free swine is a miniature swine wherein both male and female swine mated in step (a) are human-tropic PERV-positive and wherein the offspring of (a) that are mated in (b) are each human-tropic PERV-positive swine.

8. The process of claim 7 wherein said miniature swine is of the D/D haplotype.

9. The process of claim 6 wherein the swine mated in (a) are each positive for all but one human-tropic PERV-locus, said male and female so mated are each negative for a different PERV-locus, and the male and female of each mated pair of offspring mated in (b) are each, positive, if at all, for a set of human-tropic PERV-loci with no human-tropic PERV loci in common.

10. The process of claim 9 wherein step (a) comprises mating swine carrying a first set of PERVs and swine carrying a second set of PERVs wherein each of said first and second sets of PERVs comprises at least one PERV not present in the other set, to produce offspring and step (b) comprises mating offspring of (a) whereby such mating is between a first swine that carries PERVs present in both of said first and second sets of PERVs but no PERV not present in both of said first and second sets of PERVs and a second swine that carries the PERVs present in said first and second sets of PERVs but not present in both of said first and second sets of PERVs.

11. The process of claim 10 wherein said swine in step (a) carrying said first set of PERVs is a male swine and said swine in step (a) carrying said second set of PERVs is a female swine.

12. The process of claim 10 wherein said second swine in step (b) is a male swine and said first swine in step (b) is a female swine.

13. The process of claim 12 wherein said swine produced by the said process is a miniature swine.

14. The process of claim 13 wherein said miniature swine is of the D/D haplotype.

* * * * *

SEQUENCE LISTING

<160> NUMBER OF SEQ ID NOS: 34

<210> SEQ ID NO 1
<211> LENGTH: 600
<212> TYPE: DNA
<213> ORGANISM: Sus sp.

<400> SEQUENCE: 1

```
atgcatccca cgttaagccg gcgccacctc ccgattcggg gtggaaagcc gaaaagactg     60
aaaatcccct taagcttcgc ctccatcgcg tggttcctta ctctgtcaat aactcctcaa    120
gttaatggta aacgccttgt ggacagcccg aactcccata aaccctatc tctcacctgg     180 ttacttactg actccggtac aggtattaat attaacagca ctcaagggga ggctcccttg    240
gggacctggt ggcctgaatt atatgtctgc cttcgatcag taatccctgg tctcaatgac    300
caggccacac cccccgatgt actccgtgct tacgggtttt acgtttgctc aggaccccca    360
aataatgaag aatattgcgg aaatcctcag gatttctttt gcaagcaatg gagctgcgta    420
acttctaatg atgggaattg gaaatggcca gtctctcagc aagacagagt aagttactct    480
tttgttaaca atcctaccag ttataatcaa tttaattatg gccatgggag atggaaagat    540
tggcaacagc gggtacaaaa agatgtacga aataagcaaa taagctgtca ttcgttagac    600
```

<210> SEQ ID NO 2
<211> LENGTH: 600
<212> TYPE: DNA
<213> ORGANISM: Sus sp.

<400> SEQUENCE: 2

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt ggacagcccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct tacgggtttt acgtttgccc aggaccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg gccatgggag atggaaagat     540
tggcaacagc gggtacaaaa agatgtacga aataagcaaa taagctgtca ttcgttagac     600
```

<210> SEQ ID NO 3
<211> LENGTH: 540
<212> TYPE: DNA
<213> ORGANISM: Sus sp.

<400> SEQUENCE: 3

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt ggacagcccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct tacgggtttt acgtttgccc aggaccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg gccatgggag atggaaagat     540
```

<210> SEQ ID NO 4
<211> LENGTH: 600
<212> TYPE: DNA
<213> ORGANISM: Sus sp.

<400> SEQUENCE: 4

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt gaacagtccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct tacgggtttt acgtttgccc aggaccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg gccatgggag atggaaagat     540
tggcaacagc gggtacaaaa agatgtacga aataagcaaa taagctgtca ttcgttagac     600
```

<210> SEQ ID NO 5
<211> LENGTH: 599
<212> TYPE: DNA
<213> ORGANISM: Sus sp.

<400> SEQUENCE: 5

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt gaacagtccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac ccccgatgt actccgtgct tacgggtttt acgtttgccc aggaccccca      360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg gccatgggag atggaaagat     540
tggcaacagc gggtacaaaa agatgtacga aataagcaaa taagctgtca ttcgttaga      599
```

<210> SEQ ID NO 6
<211> LENGTH: 599
<212> TYPE: DNA
<213> ORGANISM: Sus sp.

<400> SEQUENCE: 6

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt gaacagtccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac ccccgatgt actccgtgct tacgggtttt acgtttgccc aggaccccca      360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg gccatgggag atggaaagat     540
tggcaacagc gggtacaaaa agatgtacga aataagcaaa taagctgtca ttcgttaga      599
```

<210> SEQ ID NO 7
<211> LENGTH: 600
<212> TYPE: DNA
<213> ORGANISM: Sus sp.

<400> SEQUENCE: 7

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt gaacagtccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac ccccgatgt actccgtgct tacgggtttt acgtttgccc aggaccccca      360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg gccatgggag atggaaagat     540
tggcaacagc gggtacaaaa agatgtacga aataagcaaa taagctgtca ttcgttagac     600
```

<210> SEQ ID NO 8
<211> LENGTH: 599
<212> TYPE: DNA
<213> ORGANISM: Sus sp.

<400> SEQUENCE: 8

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt ggacagcccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct tacgggtttt acgtttgccc aggaccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg ccatgggag atggaaagat     540
tggcaacagc gggtacaaaa agatgtacga aataagcaaa taagctgtca ttcgttaga      599
```

<210> SEQ ID NO 9
<211> LENGTH: 599
<212> TYPE: DNA
<213> ORGANISM: Sus sp.

<400> SEQUENCE: 9

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt ggacagcccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg cctcaatgac     300
caggccacac cccccgatgt actccgtgct tacgggtttt acgtttgccc aggaccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
tttgttaaca atcctaccag ttataatcaa tttaattatg ccatgggag atggaaagat     540
tggcaacagc gggtacaaaa agatgtacga aataagcaaa taagctgtca ttcgttaga      599
```

<210> SEQ ID NO 10
<211> LENGTH: 599
<212> TYPE: DNA
<213> ORGANISM: Sus sp.

<400> SEQUENCE: 10

```
atgcatccca cgttaagccg gcgccacctc ccgattcggg gtggaaagcc gaaaagactg      60
aaaatcccct taagcttcgc ctccatcgcg tggttcctta ctctgtcaat aactcctcaa     120
gttaatggta aacgccttgt ggacagcccg aactcccata aacccttatc tctcacctgg     180
ttacttactg actccggtac aggtattaat attaacagca ctcaagggga ggctcccttg     240
gggacctggt ggcctgaatt atatgtctgc cttcgatcag taatccctgg tctcaatgac     300
caggccacac cccccgatgt actccgtgct tacgggtttt acgtttgccc aggaccccca     360
aataatgaag aatattgtgg aaatcctcag gatttctttt gcaagcaatg gagctgcgta     420
acttctaatg atgggaattg gaaatggcca gtctctcagc aagacagagt aagttactct     480
```

```
tttgttaaca atcctaccag ttataatcaa tttaattatg gccatgggag atggaaagat    540
tggcaacagc gggtacaaaa agatgtacga aataagcaaa taagctgtca ttcgttaga    599

<210> SEQ ID NO 11
<211> LENGTH: 458
<212> TYPE: DNA
<213> ORGANISM: Sus sp.

<400> SEQUENCE: 11
gacagcccga actcccataa accctcatct ctcacctggt tacttactga ctccggtaca     60
ggtattaata ttaacagcac tcaaggggag gctcccttgg ggacctggtg gcctgaatta    120
tatgtctgcc ttcgatcagt aatccctggt ctcaatgacc aggccacacc ccccgatgta    180
ctccgtgctt acgggtttta cgtttgccca ggaccccccaa ataatgaaga atattgtgga   240
aatcctcagg atttcttttg caagcaatgg agctgcgtaa cttctaatga tgggaattgg    300
aaatggccag tctctcagca agacagagta agttactctt ttgttaacaa tcctacctat    360
aataatcaat ttaattatgg ccatgggaga tggaaagatt ggcaacagcg ggtacaaaaa    420
gatgtacgaa ataagcaaat aagctgtcat tcgttaga                           458

<210> SEQ ID NO 12
<211> LENGTH: 478
<212> TYPE: DNA
<213> ORGANISM: Sus sp.

<400> SEQUENCE: 12
ttaatggtaa acgccttgtg gacagcccga actcccataa acccttatct ctcacctggt     60
tacttactga ctccggtaca ggtattaata ttaacagcac tcaaggggag gctcccttgg    120
ggacctggtg gcctgaatta tatgtctgcc ttcgatcagt aatccctggt ctcaatgacc    180
aggccacacc ccccgatgta ctccgtgctt acgggtttta cgtttgccca ggaccccccaa   240 ataatgaaga atattgtgga aatcctcagg atttcttttg caggcaatgg agctgcgtaa    300
cttctaatga tgggaattgg aaatggccag tctctcagca agacagagta agttactctt    360
ttgttaacaa tcctaccagt tataatcaat ttaattatgg ccatgggaga tggaaagatt    420
ggcaacagcg ggtacaaaaa gatgtacgaa ataagcaaat aagctgtcat tcgttaga     478

<210> SEQ ID NO 13
<211> LENGTH: 478
<212> TYPE: DNA
<213> ORGANISM: Sus sp.

<400> SEQUENCE: 13
ttaatggtaa acgccttgtg gacagcccga actcccataa acccttatct ctcacctggt     60
tacttactga ctccggtaca ggtattaata ttaacagcac tcaaggggag gctcccttgg    120
ggacctggtg gcctgaatta tatgtctgcc ttcgatcagt aatccctggt ctcaatgacc    180
aggccacacc ccccgatgta ctccgtgctt acgggtttta cgtttgccca ggaccccccaa   240 ataatgaaga atattgtgga aatcctcagg atttcttttg caagcaatgg agctgcgtaa    300
cttctaatga tgggaattgg aaatggccag tctctcagca agacagagta agttactctt    360
ttgttaacaa tcctaccagt tataatcaat ttaattatgg ccatgggaga tggaaagatt    420
ggcaacagcg ggtacaaaaa gatgtacgaa ataagcaaat aagctgtcat tcgttaga     478

<210> SEQ ID NO 14
```

-continued

```
<211> LENGTH: 458
<212> TYPE: DNA
<213> ORGANISM: Sus sp.

<400> SEQUENCE: 14
gacagcccga actcccataa acccttatct ctcacctggt tacttactga ctccggtaca    60
ggtattaata ttaacagcac tcaaggggag gctcccttgg ggacctggtg gcctgaatta   120
tatgtctgcc ttcgatcagt aatccctggt ctcaatgacc aggccacacc ccccgatgta   180
ctccgtgctt acgggtttta cgtttgccca ggacccccaa ataatgaaga atattgtgga   240
aatcctcagg atttcttttg caagcaatgg agctgcgtaa cttctaatga tgggaattgg   300
aaatggccag tctctcagca agacagagta agttactctt tgttaacaa tcctaccagt   360
tataatcaat ttaattatgg ccatgggaga tggaaagatt ggcaacagcg ggtacaaaaa   420
gatgtacgaa ataagcaaat aagctgtcat tcgttaga                           458

<210> SEQ ID NO 15
<211> LENGTH: 478
<212> TYPE: DNA
<213> ORGANISM: Sus sp.

<400> SEQUENCE: 15
ttaatggtaa acgccttgtg gacagcccga actcccataa acccttatct ctcacctggt    60
tacttactga ctccggtaca ggtattaata ttaacagcac tcaagaggag gctcccttgg   120
ggacctggtg gcctgaatta tatgtctgcc ttcgatcagt aatccctggt ctcaatgacc   180
aggccacacc ccccgatgta ctccgtgctt acgggtttta cgtttgccca ggacccccaa   240
ataatgaaga atattgtgga aatcctcagg atttcttttg caagcaatgg agctgcgtaa   300
cttctaatga tgggaattgg aaatggccag tctctcagca agacagagta agttactctt   360
ttgttaacaa tcctaccagt tataatcaat ttaattatgg ccatgggaga tggaaagatt   420
ggcaacagcg ggtacaaaaa gatgtacgaa ataagcaaat aagctgtcat tcgttaga    478

<210> SEQ ID NO 16
<211> LENGTH: 478
<212> TYPE: DNA
<213> ORGANISM: Sus sp.

<400> SEQUENCE: 16
ttaatggtat gcgccttgtg gactgcccga actcccataa acccttatct ctcacctggt    60
tacttactga ctccggtaca ggtattaata ttaacatcac tcaaggggag gctcccttgg   120
ggacctggtg gcctgaatta tatgtctgcc ttcgatcagt aatccctggt ctcaatgacc   180
aggccacacc ccccgatgta ctccgtgctt acgggtttta cgtttgccca ggacccccaa   240
ataatgaaga atattgtgga aatcctcagg atttcttttg caagcaatgg agctgcgtaa   300
cttctaatga tgggaattgg aaatggccag tctctcagca agacagagta agttactctt   360
ttgttaacaa tcctaccagt tataatcaat ttaattatgg ccatgggaga tggaaagatt   420
ggcaacagcg ggtacaaaaa gatgtacgaa ataagcaaat aagctgtcat tcgttaga    478

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.
```

-continued

```
<400> SEQUENCE: 17
gtgtgttctg gatctgttgg tttc                                          24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 18
ccacgcaggg gtagaggact                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 19
ctaggaggat cacaggctgc                                               20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 20
cctggtggtc tcctactgtc g                                             21

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 21
gtgtgtctgg atctgttggt ttc                                           23

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 22
tgcctgcttg tggaagacg                                                19

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 23
```
gcttttatgg ggttcacaac aaa               23

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 24
ccacgcaggg gtagaggact               20

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 25
cctaccagtt ataatcaatt taattatggc               30

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 26
aggttgtatt gtaatcagag ggg               23

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 27
cgtggttcct tactctgtca ataactc               27

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 28
ctaatgatgg gaattggaaa tgg               23

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 29

```
gctyacccctt actgaggttt ctgg                                             24

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 30
ggacttagta acctacatcg aattgtaac                                         29

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 31
ccaacaagaa gaggtagcct ctg                                               23

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 32
ggatcttccg ttacaattcg atgtag                                            26

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 33
tctcgtactt tttgaccaca ccaacg                                            26

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Primer
      sequence used in amplification of PERV-sequences.

<400> SEQUENCE: 34
gcttaccctt actgaggttt ctgg                                              24
```